US012748041B2

(12) United States Patent
Cox et al.

(10) Patent No.: US 12,748,041 B2
(45) Date of Patent: Sep. 29, 2026

(54) APPARATUS AND METHOD FOR TESTING BLOOD

(71) Applicant: Siemens Healthcare Diagnostics Inc., Tarrytown, NY (US)

(72) Inventors: Janine Cox, Stoughton, MA (US); Justin DeSilva, Mendon, MA (US); Justin Davis, Raleigh, NC (US); Michael Chen, Sharon, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 19/149,214

(22) PCT Filed: Jan. 24, 2024

(86) PCT No.: PCT/US2024/012756
§ 371 (c)(1),
(2) Date: Jul. 18, 2025

(87) PCT Pub. No.: WO2024/158897
PCT Pub. Date: Aug. 2, 2024

(65) Prior Publication Data

US 2026/0118257 A1 Apr. 30, 2026

Related U.S. Application Data

(60) Provisional application No. 63/481,831, filed on Jan. 27, 2023.

(51) Int. Cl.
*G01N 21/29* (2006.01)
*B01L 3/00* (2006.01)
(Continued)

(52) U.S. Cl.
CPC .......... *G01N 21/293* (2013.01); *B01L 3/5023* (2013.01); *G01N 21/01* (2013.01);
(Continued)

(58) Field of Classification Search
CPC ...... G01N 21/293; G01N 21/01; G01N 21/78; G01N 33/491; G01N 33/52; G01N 21/525;
(Continued)

(56) References Cited

U.S. PATENT DOCUMENTS 6,069,014 A * 5/2000 Schrier ............ G01N 33/54389 436/514
7,598,090 B2 * 10/2009 Takahashi ........ G01N 33/54388 435/7.1
(Continued)

FOREIGN PATENT DOCUMENTS

EP 0353500 A2 * 2/1990 ........... G01N 33/558
JP 2005506541 A * 3/2005 ............ B01L 3/5027
(Continued)

OTHER PUBLICATIONS

International Search Report and Written Opinion of International Application No. PCT/US2024/012756 mailed on Apr. 19, 2024.
(Continued)

*Primary Examiner* — Abdullahi Nur

(57) ABSTRACT

An apparatus comprises a barrel and a colorimetric assay assembly. The barrel has a sidewall defining a portion of a colorimetric chamber that is in fluid communication with an internal chamber defined by an inner surface. The colorimetric assay assembly, housed in the colorimetric chamber, comprises a sample application pad to receive a fluid sample and a colorimetric detection pad to visualize a presence of free hemoglobin. The sample application pad is formed of a prefiltration layer and a filtration layer. The prefiltration layer comprises a distal surface having a first wetting property and a hydrophilic receiving surface having a second wetting property less than the first wetting property and is configured to receive the fluid sample and convey at least a portion of the fluid sample to the filtration layer. The filtration layer is porous to plasma and the free hemoglobin and not porous to red blood cells.

20 Claims, 11 Drawing Sheets

(51) Int. Cl.
*G01N 21/01* (2006.01)
*G01N 33/49* (2006.01)

(52) U.S. Cl.
CPC .... *G01N 33/491* (2013.01); *B01L 2300/0681* (2013.01); *B01L 2300/161* (2013.01); *B01L 2400/0406* (2013.01)

(58) Field of Classification Search
CPC .................... G01N 21/50; B01L 3/5023; B01L 2300/0681; B01L 2300/161; B01L 2400/0406; A61B 5/15
See application file for complete search history.

(56) References Cited

U.S. PATENT DOCUMENTS

| | | | |
|---|---|---|---|
| 2013/0040333 | A1 | 2/2013 | Karlsson |
| 2013/0217054 | A1 | 8/2013 | Huffstodt et al. |
| 2014/0329268 | A1 | 11/2014 | Karlsson |
| 2022/0236293 | A1 | 7/2022 | Forzani et al. |

FOREIGN PATENT DOCUMENTS

| | | | | |
|---|---|---|---|---|
| WO | WO-9635952 | A1 * | 11/1996 | ........... G01N 33/491 |
| WO | 2011155897 | A1 | 12/2011 | |
| WO | 2012143894 | A1 | 10/2012 | |
| WO | 2013085462 | A1 | 6/2013 | |
| WO | 2015191450 | A1 | 12/2015 | |
| WO | 2017133953 | A1 | 8/2017 | |
| WO | 2020118021 | A1 | 6/2020 | |
| WO | 2021205228 | A1 | 10/2021 | |
| WO | 2021262061 | A1 | 12/2021 | |
| WO | 2023019085 | A1 | 2/2023 | |
| WO | 2023019086 | A1 | 2/2023 | |
| WO | 2023019088 | A1 | 2/2023 | |
| WO | 2023245072 | A2 | 12/2023 | |

OTHER PUBLICATIONS

Pall Life Sciences—"Glass Fiber Media (Hydrophilic)"—Product Information, (Excerpt) pp. 80-81. No publication date is shown. Only a 2-page excerpt is available to the applicant.

* cited by examiner

APPARATUS AND METHOD FOR TESTING BLOOD

This application claims benefit under 35 USC § 119(e) of U.S. Provisional Application No. 63/481,831, filed Jan. 27, 2023. The entire contents of the above-referenced patent application are hereby expressly incorporated herein by reference.

DESCRIPTION OF THE PRIOR ART

Blood sampling is a common health care procedure typically used in hospital and laboratory settings to determine the physiological and biochemical condition of a patient. Blood sampling is essential to the diagnosis and treatment of patients suspected of a wide variety of disorders. Blood samples are analyzed by fluid testing devices, such as blood analyzers, to detect clinically significant variations in blood components, e.g., plasma, red blood cells, white blood cells, and platelets, or other characteristics, such as blood gas, co-oximetry, and electrolytes. Analysis of these parameters, can aid in the diagnosis of electryly and metabolity imbalance, oxygen delivery capacity and the acid-base status of a patient, which may indicate particular pathological conditions or stage of disease progression.

Plasma is normally colorless or light yellow. However, if the red blood cells have been ruptured (hemolyzed), the release of hemoglobin will cause the plasma to appear from light pink to dark maroon, depending on the level of hemolysis. Hemolysis in a blood sample is typically time consuming to detect. Typically, a user would have to centrifuge the sample, and compare the plasma color to a hemolytic index or to test plasma on the analyzer. This requires access to expensive equipment, such as a centrifuge, and takes time. On the other hand, testing without checking for hemolysis can result in lengthier delays, as an unexpected high potassium could place doubt on the entire test result, leading to a treatment delay and increase in cost while a repeat sample is drawn and tested.

A need exists for an apparatus and method that enables more rapid hemolysis detection. It is to such an apparatus and method that the inventive concepts disclosed and claimed herein are directed.

SUMMARY OF THE INVENTION

The inventive concepts disclosed and claimed herein generally relate to an apparatus comprising a barrel and a colorimetric assay assembly. The barrel has a first end, a second end opposite the first end, a sidewall extending between the first end and the second end, and an inner surface defining an internal chamber, the sidewall defining at least a portion of a colorimetric chamber in fluid communication with the internal chamber via a passage through the sidewall of the barrel.

The colorimetric assay assembly is housed in the colorimetric chamber and is configured to detect the presence of free hemoglobin in a fluid sample. The colorimetric assay assembly comprises a sample application pad configured to receive the fluid sample from the internal chamber. The sample application pad is formed of a prefiltration layer of a prefiltration material and a filtration layer of a filtration material. The prefiltration layer comprises a distal surface having a first wetting property and a hydrophilic receiving surface having a second wetting property less than the first wetting property. The hydrophilic receiving surface is configured to receive the fluid sample and convey at least a portion of the fluid sample to the filtration layer. The filtration layer is porous to plasma and the free hemoglobin and not porous to red blood cells. The colorimetric detection pad is in fluidic contact with the sample application pad and is configured to visualize a change of color due to a presence of the free hemoglobin.

In another aspect, the inventive concepts disclosed and claimed herein generally relate to a kit, comprising the apparatus discussed above and a reference device containing a plurality of reference colors. Each reference color corresponds to a different level of free hemoglobin.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings.

DETAILED DESCRIPTION

Figure 1:
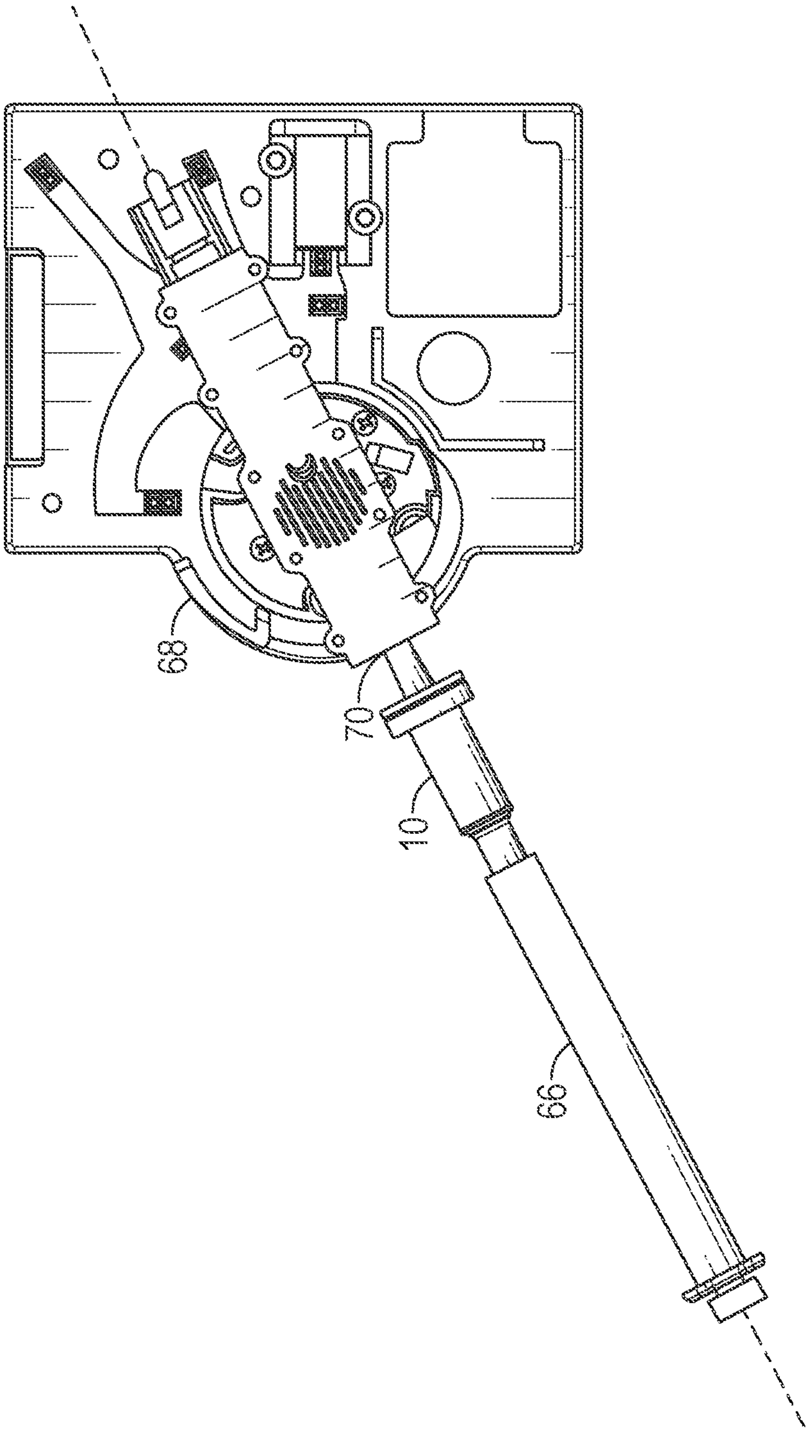
FIG. 1 is a side perspective view of an exemplary embodiment of an apparatus according to the inventive concepts disclosed herein shown coupled to a sample receiving assembly.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. The language used herein is intended to be given the broadest possible scope and meaning; and the embodiments are meant to be exemplary-not exhaustive. Also, it is to be understood that the phraseology and terminology employed herein is for the purpose of description and should not be regarded as limiting.

Independent of the grammatical term usage, individuals with male, female or other gender identities are included within the term.

Unless otherwise defined, scientific and technical terms used in connection with the presently disclosed and claimed inventive concept(s) shall have the meanings commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All the articles, compositions and/or methods disclosed and claimed herein can be made and executed without undue experimentation, given the present disclosure. While the articles, compositions and methods of the inventive concept(s) have been described in terms of preferred embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized under the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the inherent variation of error for the device, the method being employed to determine the value, or the variation that exists among the study subjects.

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

In the following detailed description of embodiments of the inventive concept, numerous specific details are set forth in order to provide a more thorough understanding of the inventive concept. However, it will be apparent to one of ordinary skill in the art that the inventive concept within the disclosure may be practiced without these specific details. In other instances, well-known features have not been described in detail to avoid unnecessarily complicating the instant disclosure.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Described herein, and shown in the accompanying figures, are several non-limiting embodiments of apparatus of the presently claimed and disclosed inventive concepts which may be used in association with collection syringes and liquid sample analyzers. The fluid sample is generally from a biological source. A "fluid" refers to any substance that has no fixed shape and yields easily to external pressure.

Figure 3:
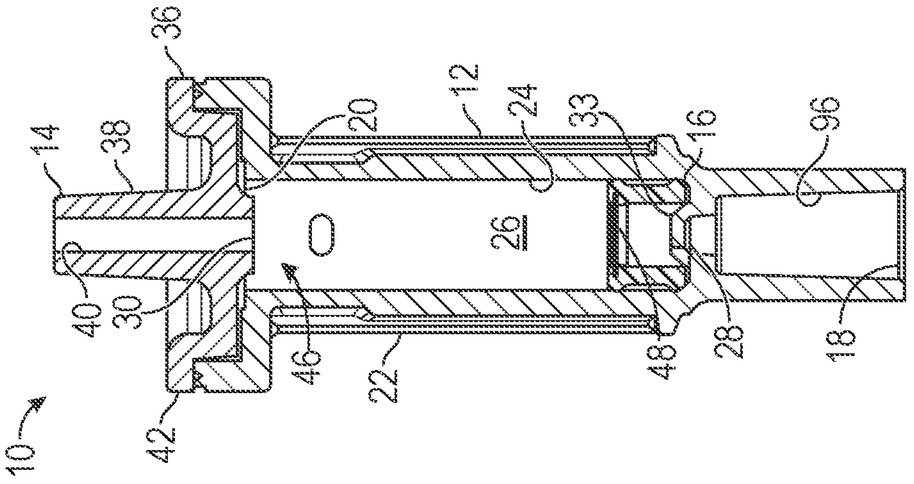
FIG. 3 is a longitudinal, cross-sectional view of the apparatus of FIG. 1 illustrating a position of the filter member prior to removal of bubbles from the fluid sample.

Referring now to the drawings, and more particularly to FIGS. 1-3, shown therein is an exemplary embodiment of an apparatus 10 for transferring a fluid sample from a liquid sample collection apparatus to a liquid sample analyzer and for removing bubbles from the fluid sample constructed in accordance with the inventive concepts disclosed and claimed herein. The apparatus 10 includes a barrel 12, a nozzle cap 14, and a filter member 16.

The barrel 12 includes a first end 18, a second end 20, a sidewall 22, and an inner surface 24. The barrel 12 may be of any suitable size and shape, and formed of any suitable material, such as, without limitation, plastics such as polycarbonate, polystyrene, polyacrylates, and polyurethane, or medical-grade polymers. The sidewall 22 of the barrel 12 extends between the first end 18 and the second end 20 of the barrel 12. The inner surface 24 of the barrel 12 defines an internal chamber 26. The first end 18 has an inlet opening 28 and the second end 20 has an outlet opening 30.

The internal chamber 26 may be of any suitable size and shape to contain a fluid sample 32. The fluid sample 32 may be a liquid biological sample, for example, blood, serum, plasma, or other bodily fluids. The fluid sample 32 may contain a gas portion and a liquid portion. The gas portion of the fluid sample 32 may be, for example, air or other gases. A portion of the gas portion may form bubbles in the fluid sample.

The inlet opening 28 and the outlet opening 30 may have a cross-section of any suitable geometry, including, but not limited to, circular, oval, square, or rectangular. The inlet opening 28 and the outlet opening 30 may be molded or cut into the barrel 12, or otherwise pre-fabricated. The inlet opening 28 may be formed to capture clots as the fluid sample 32 is passed into the internal chamber 26 via the inlet opening 28.

Figure 2B:
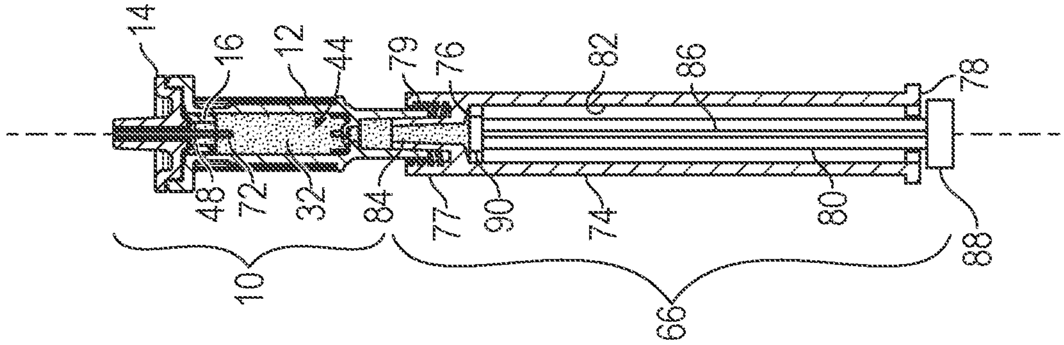
FIG. 2B is a longitudinal, cross-sectional view of the apparatus of FIG. 1 coupled to a collection syringe illustrating the insertion of a probe into the apparatus following removal of bubbles from of the fluid sample.

The outlet opening 30 may be provided with a nozzle cap 14. The nozzle cap 14 includes an annular wall 36 and a tubular portion 38 having a bore 40 extending therethrough. The tubular portion 38 may be in the form of a male luer for frictional engagement with a portion of a liquid sample analyzer 68 (FIG. 1). The liquid sample analyzer 68 includes a sample input port 70 for frictionally receiving the tubular portion 38 and a sample probe 72 (FIGS. 2B and 3). The sample probe 72 may be axially slidable relative to the sample input port 70. The bore 40 may have a cross-section of any suitable geometry, including, but not limited to, circular, oval, square, or rectangular. The bore 40 may be sized to have a diameter adapted to slidably axially receive a sample probe. The base of the tubular portion 38 flares outwardly and merges with the annular wall 36 at a rim 42, the annular wall 36 tapers downwardly to form an inverted frusto-conical section. The nozzle cap 14 may be releasably coupled to the outlet opening 30 such that the bore 40 is aligned with the outlet opening 30 to permit fluid communication with the internal chamber 26.

The filter member 16 is disposed within the internal chamber 26 so the filter member 16 defines an inlet side 44 and an outlet side 46 of the internal chamber 26. The filter member 16 is positionable between the first end 18 and the second end 20 of the barrel 12. The filter member 16 includes at least one gas-permeable, liquid-impermeable membrane 48. The filter member 16 may be any suitable shape and size to sealingly engage the inner surface 24 of the barrel 12. The filter member 16 may be formed of any suitable material, such as, without limitation, a rubber, an elastomer, a polyolefin-based resin, a fluorine-based resin, or a polyester-based resin. The elastomer may include, for example, a polyvinyl chloride-based elastomer, a polyolefin-based elastomer, a styrene-based elastomer, a polyester-based elastomer, a polyamide-based elastomer, a polyurethane-based elastomer, or a mixture thereof.

The at least one gas-permeable, liquid-impermeable membrane 48 may be formed of any suitable material, such as, without limitation, polytetrafluoroethylene, polyvinylidene fluoride, polyvinylchloride, polyolefins like polypropylene, polyethylene, polymethylpentene, polyamides, polysulfones, polyetheretherketones, polycarbonates, and combinations including any of these. In one embodiment, the gas-permeable, liquid-impermeable membrane 48 is formed from a material comprising at least one of polytetrafluorethylene, polypropylene, and polyethylene. The at least one gas-permeable, liquid-impermeable membrane 48 may have a thickness suitable for allowing puncture upon application of a mechanical force. The at least one gas-permeable, liquid-impermeable membrane 48 may permit at least a portion of the gas portion of the fluid sample 32, which forms bubbles, to pass across the filter member 16 from the inlet side 44 to the outlet side 46 of the internal chamber 26. The at least one gas-permeable, liquid-impermeable membrane 48 also provides a fluid-tight seal across the filter member 16 to prevent the liquid portion of the fluid sample 32 from passing from inlet side 44 to the outlet side 46 as the fluid sample 32 is passed into the internal chamber 26 via the inlet opening 28 to separate at least a portion of the gas portion from the liquid portion of the fluid sample 32. The filter member 16 is pierceable so a sample probe 72 may be passed through the filter member 16 from the outlet side 46 to the inlet side 44 to withdraw the liquid portion of the fluid sample 32 from the inlet side 44 of the internal chamber 26.

As shown in FIG. 1, the apparatus 10 may be used in association with a fluid sample collection apparatus, such as a collection syringe 66 and the liquid sample analyzer 68 for transferring a fluid sample from the collection syringe 66 to the liquid sample analyzer 68 and to remove bubbles from the fluid sample 32 having a liquid portion and a gas portion. Although, FIG. 1 shows the apparatus 10 associated with the collection syringe 66 and the liquid sample analyzer 68, those skilled in the art will understand and appreciate that the apparatus 10 may independently be associated with collection devices other than the collection syringe 66, such as, for example, a vacuum tube, and medical devices other than the liquid sample analyzer 68. The liquid sample analyzer 68 may be any suitable fluid testing device, such as, without limitation, microfluidic devices, blood gas analyzers, hematology analyzers, urine chemistry analyzers, and the like.

The liquid sample analyzer 68 includes the sample input port 70 and a sample probe 72 (FIG. 2B). The sample input port 70 may be sized (e.g., a female luer) to frictionally receive and detachably secure at least a portion of the nozzle cap 14, as shown in FIG. 1 to permit "hands-free" operation of the liquid sample analyzer 68 in a way that the fluid sample in the apparatus 10 may be drawn into the liquid sample analyzer 68 via the sample probe 72 without a user holding the apparatus 10.

The sample probe 72 may be extended to pass through the filter member 16 from the outlet side 46 of the internal chamber 26 to the inlet side 44 to withdraw at least a portion of the fluid sample 32 into the liquid sample analyzer 68 from the inlet side 44 of the internal chamber 26, as shown in FIG. 2B. The sample probe 72 may be of a length compatible with sampling from the inlet side 44 of the internal chamber 26.

The collection syringe 66 includes a syringe body 74 having a front end 76, a rear end 78, and a plunger 80. The syringe body 74 defines a reservoir 82 within which the fluid sample 32 may be contained and later expelled via a dispensing opening 84 positioned at the front end 76 of the syringe body 74. The rear end 78 of the syringe body 74 may be open and provided with a body flange 85 to facilitate the collection and expulsion of the fluid sample 32. The syringe body 74 may be any suitable size or shape for collection of fluid samples, such as, for example, a cylindrical shape. The syringe body 74 may also include a collar 77 formed concentrically with the dispensing opening 84 into a cylindrical shape to surround the dispending opening 84. The collar 77 may include an inner peripheral surface in which a threaded engagement portion 79 is formed for engaging the apparatus 10. The syringe body 74 may be constructed of any suitable material, such as glass or plastic. The syringe body 74 may have an outer diameter adapted to coaxially slide within the first end 18 of the apparatus 10.

The plunger 80 may include a shaft 86 that terminates at one end in a plunger flange 88 to facilitate the collection and expulsion of the fluid sample 32. The shaft 86 may, for example, have a cylindrical shape or a columnar shape, and may have a cross-section of a polygonal shape, such as a square, pentagonal, hexagonal, or cruciform shape. The plunger 80 may further include a plunger seal 90 secured to the shaft 86 opposite the plunger flange 88. The plunger 80 may be removably disposed within the syringe body 74 and may be selectively movable within the reservoir 82. The plunger seal 90 has a diameter that permits the plunger seal 90 to create a fluid-tight seal when positioned within the reservoir 82 such that the fluid sample 32 may not move past the plunger seal 90. Further, the plunger seal 90 prevents ambient air from moving from the rear end 78 of the syringe body 74 in a direction past the plunger seal 90. The plunger 80 may be axially displaced relative to the syringe body 74. Movement of the plunger 80 from the rear end 78 to the front end 76 of the syringe body 74 may cause at least a portion of the fluid sample 32 to be expelled from the reservoir 82 and introduced into the inlet opening 28 of the apparatus 10 via the dispensing opening 84. The plunger 80 may be constructed of any suitable polymeric material known in the art.

Figure 2A:
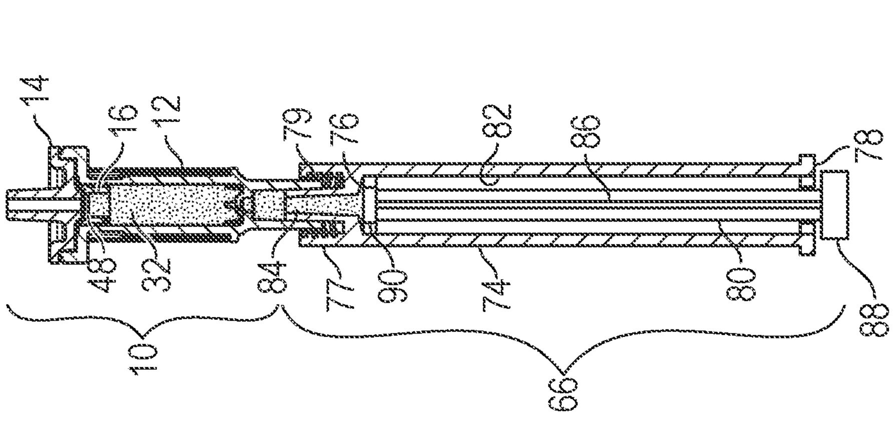
FIG. 2A is a longitudinal, cross-sectional view of the apparatus of FIG. 1 coupled to a collection syringe illustrating positioning of the filter member and plunger assembly following removal of bubbles from the fluid sample.

To remove the gas portion (i.e., bubbles) of the fluid sample 32 from the liquid portion, the collection syringe 66, containing a volume of the fluid sample 32 within the reservoir 82, is releasably attached to the first end 18 of the barrel 12, as shown in FIG. 2A. As shown in FIGS. 2A-2B, the front end 76 of the syringe body 74 may be interlockingly engaged with the apparatus 10 by way of the threaded engagement portion 79.

As shown in FIGS. 2A-2B, the threaded engagement portion 79 may interlockingly engage the barrel connection portion 94 such that significant relative movement between the collection syringe 66 and the apparatus 10 is prevented to permit "hands-free" operation of the liquid sample analyzer in a way that the fluid sample from in the collection syringe 66 may be drawn into the liquid sample analyzer via the apparatus 10 without a user holding the collection syringe 66 or the apparatus 10. It will be appreciated that other suitable connectors may be utilized between the apparatus 10 and collection syringe 66, such as a luer slip connection. The first end 18 of the barrel 12 may include a female luer 96 (FIG. 3).

In use, the collection syringe 66 and the apparatus 10 are positioned in an upright orientation with the apparatus 10 above the collection syringe 66 and the bubbles in the fluid sample rise to the top of the fluid sample. The plunger 80 of the collection syringe 66 is displaced axially along the reservoir 82 a distance from the rear end 78 towards the front end 76 of the syringe body 74, as shown in FIG. 2A. Movement of the plunger 80 within the reservoir 82 causes at least a portion of the gas portion (i.e., bubbles) of the fluid sample 32 to be expelled from the reservoir 82 and into the internal chamber 26 of the apparatus 10 via the inlet opening 28 and a clot catcher 33, passing through the filter member 16. The gas portion of the fluid sample 32 passes through the filter member 16, and is then ultimately expelled from the internal chamber 26 of the apparatus 10. Once, at least a portion of the gas portion of the fluid sample 32 has been displaced from the reservoir 82, the plunger 80 experiences an initial resistive force.

Upon application of sufficient force to overcome the initial resistive force, the plunger 80 is advanced further into the reservoir 82 towards the front end 76 of the syringe body 74, as shown in FIG. 2B, thereby increasing the internal pressure of the reservoir 82. As the internal pressure of the reservoir 82 increases, it produces a force sufficient to cause at least a portion of the liquid portion of the fluid sample 32 to be expelled from the reservoir 82 and into the internal chamber 26 of the barrel 12 via the inlet opening 28. The fluid sample 32 entering the internal chamber 26 may cause the filter member 16 to be displaced axially along the internal chamber 26 towards the second end 20 of the barrel 12, as shown in FIG. 2B. The filter member 16 may be displaced such that the gas-permeable, liquid-impermeable membrane 48 of the filter member 16 becomes disposed adjacent the outlet opening 30. This arrangement prevents the fluid sample 32 from exiting the internal chamber 26 via the outlet opening 30. In some embodiments, the plunger 80 may be partially extended into the reservoir 82 so less than all of the fluid sample 32 is transferred from the reservoir 82 into the internal chamber 26.

Once the liquid portion of the fluid sample 32 has been expelled from the reservoir 82 and is contained within the internal chamber 26 of the apparatus 10, the sample probe 72 of the liquid sample analyzer 68 may be extended from the sample input port 70 and passed through the filter member 16 to withdraw the liquid portion of the fluid sample 32 from the inlet side 44 of the internal chamber 26. In one embodiment, the sample probe 72 pierces the gas-permeable, liquid-impermeable membrane 48 of the filter member 16 to gain fluid access to the inlet side 44 of the internal chamber 26.

After initial insertion of the apparatus 10 into the sample input port 70 by a user, no additional support is required as the fluid sample is drawn into the liquid sample analyzer 68. The connections between the collection syringe 66, the apparatus 10, and the liquid sample analyzer 68 are sufficiently rigid to prevent gravity from tilting down or putting undue stress on the combination of the connected elements such that a hands-free operation can be performed without additional supporting structures to hold the connected elements together in proper alignment. In one non-limiting embodiment and as illustrated in FIG. 1, the connections between the collection syringe 66, the apparatus 10, and the liquid sample analyzer 68 are sufficiently rigid to support the collection syringe 66 and the apparatus 10 in an axially aligned relationship with the sample probe 72 of the liquid sample analyzer 68. As such, the user need not remain at the liquid sample analyzer 68 and need not hold the apparatus 10 and/or the collection syringe 66 while a fluid sample in the apparatus 10 is drawn into the liquid sample analyzer 68 via the sample probe 72.

Figure 4A:
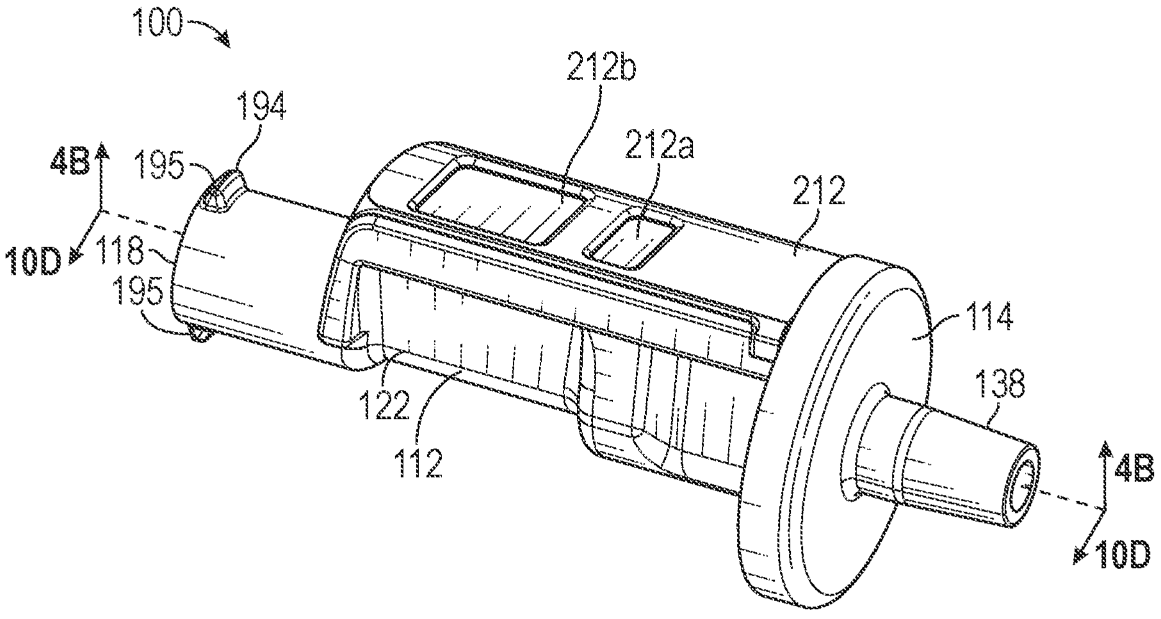
FIG. 4A is a perspective view of another exemplary embodiment of an apparatus according to the inventive concepts disclosed herein.
Figure 4B:
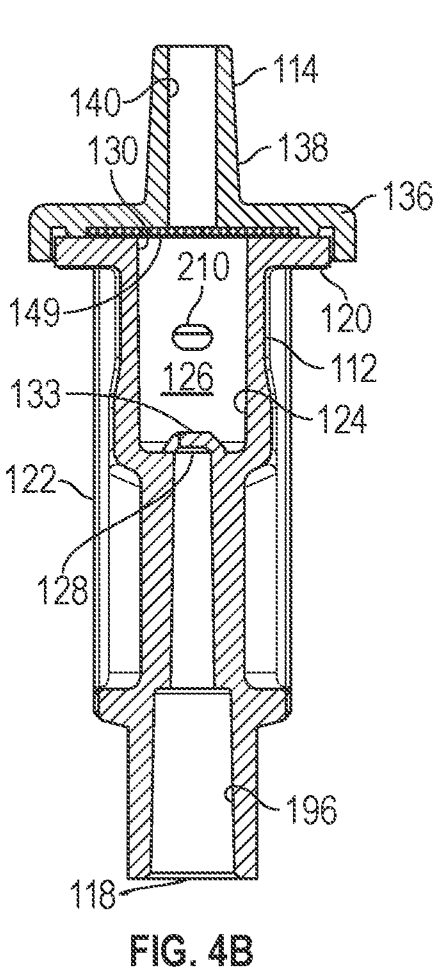
FIG. 4B is a cross-sectional view taken along line 4B-4B of FIG. 4A.

Referring now to FIGS. 4A-B, shown is another exemplary embodiment of an apparatus 100 constructed in accordance with the inventive concepts disclosed and claimed herein. The apparatus 100 is similar to the apparatus 10 described above, except as described below. The apparatus 100 includes a barrel 112 and a nozzle cap 114. The apparatus 100 is shown without a filter member 16, which is optional.

The barrel 112 includes a first end 118, a second end 120, a sidewall 122, and an inner surface 124. The barrel 112 may be of any suitable size and shape, and formed of any suitable material, such as, without limitation, plastics such as polycarbonate, polystyrene, polyacrylates, and polyurethane, or medical-grade polymers. The sidewall 122 of the barrel 112 extends between the first end 118 and the second end 120 of the barrel 112. The inner surface 124 of the barrel 112 defines an internal chamber 126. The first end 118 has an inlet opening 128 and the second end 120 has an outlet opening 130.

The internal chamber 126 may be of any suitable size and shape to contain a fluid sample, (e.g., fluid sample 32 shown in FIGS. 2A-2B). The fluid sample may be, for example, blood, serum, plasma, or other bodily fluids. The fluid sample may contain a gas portion and a liquid portion. The gas portion of the fluid sample may be, for example, air or other gases. A portion of the gas portion may form bubbles in the fluid sample.

The inlet opening 128 and the outlet opening 130 may have a cross-section of any suitable geometry, including, but not limited to, circular, oval, square, or rectangular. The inlet opening 128 and the outlet opening 130 may be molded or cut into the barrel 112, or otherwise pre-fabricated. The inlet opening 128 may be formed to capture clots as the fluid sample 32 is passed into the internal chamber 126 via the inlet opening 128. The barrel 112 may include a clot catcher 133 disposed across the inlet opening 128 so as to define a plurality of apertures that are sized and shaped to allow fluid to pass through into the internal chamber 126, but to catch or prevent solids (i.e., clots) that are larger than a predetermined size to pass through into the internal chamber 126. The solids that may be caught by the clot catcher 133 and prevented from flowing into the internal chamber 126 may include clots and other solids present in the fluid sample 32 that have the predetermined size of, for example, at least about 0.17+/−0.05 mm in diameter or larger. In one non-limiting embodiment, the clot catcher 133 is star-shaped so as to cooperate with the inlet opening 128 to define five apertures 135 through which fluid is passed through into the internal chamber 126. In this non-limiting embodiment, the five apertures 135 are formed in between five arms of the star-shaped clot catcher 133, where the size and shape of the arms may act as catching elements to catch and prevent clots from passing into the internal chamber 126.

The outlet opening 130 may be provided with the nozzle cap 114. The nozzle cap 114 includes a cap portion 136 and a tubular portion 138 having a bore 140 extending therethrough. The tubular portion 138 may be in the form of a male luer for frictional engagement with the sample input port 70 of the liquid sample analyzer 68 (FIG. 1) to permit "hands-free" operation of the liquid sample analyzer 68 in way that the fluid sample in the apparatus 100 may be drawn into the liquid sample analyzer 68 without a user holding the apparatus 100.

The bore 140 may have a cross-section of any suitable geometry, including, but not limited to, circular, oval, square, or rectangular. The bore 140 may be sized to have a diameter adapted to slidably axially receive the sample probe 72. The base of the tubular portion 138 flares outwardly and merges with the cap portion 136. The nozzle cap 114 may be coupled to the second end of the barrel 112 in a suitable manner such that the bore 140 is aligned with the outlet opening 130 to permit fluid communication with the internal chamber 126.

A gas-permeable, liquid-impermeable membrane 149 (FIG. 4B) may be secured to the barrel 112 adjacent the second end 120 of the barrel 112 to provide a fluid-tight seal across the outlet opening 130 to prevent the liquid portion of the fluid sample from passing into the outlet opening 130 from the internal chamber 126. The gas-permeable, liquid-impermeable membrane 149 is pierceable so the sample probe 72 may be passed through the gas-permeable, liquid-impermeable membrane 149 to withdraw the liquid portion of the fluid sample from the internal chamber 126.

The gas-permeable, liquid-impermeable membrane 149 may be formed of any suitable material, such as, without limitation, polytetrafluoroethylene, polyvinylidene fluoride, polyvinylchloride, polyolefins like polypropylene, polyethylene, polymethylpentene, polyamides, polysulfones, polyetheretherketones, polycarbonates, and combinations including any of these. In one embodiment, the gas-permeable, liquid-impermeable membrane 149 is formed from a material comprising at least one of polytetrafluorethylene, polypropylene, and polyethylene. The gas-permeable, liquid-impermeable membrane 149 may have a thickness suitable for allowing puncture upon application of a mechanical force.

Similar to the apparatus 10, the apparatus 100 may be used in association with the collection syringe 66 and the liquid sample analyzer 68.

To establish fluid communication between the collection syringe 66 and the apparatus 100, the collection syringe 66, containing a volume of the fluid sample within the reservoir 82, may be interlockingly engaged with the first end 118 of the barrel 112. The front end 76 of the syringe body 74 may be interlockingly engaged with the apparatus 100 by way of the threaded engagement portion 79. As shown in FIG. 4A, the barrel 112 may include a barrel connection portion 194. In one embodiment, the threaded engagement portion 79 of the syringe body 74 is a male luer connector and the barrel connection portion 194 is a female luer connector including in one exemplary embodiment a pair of thread lugs 195 extending radially from the exterior of the barrel 112 and having a thread pitch, size, and geometry corresponding to threaded engagement portion 79 of the syringe body 74. The threaded engagement portion 79 may interlockingly engage the barrel connection portion 194 such that significant relative movement between the collection syringe 66 and the apparatus 100 is prevented to permit "hands-free" operation of the liquid sample analyzer 68 in way that the fluid sample from in the collection syringe 66 may be drawn into the liquid sample analyzer 68 via the apparatus 100 without a user holding the collection syringe 66 or the apparatus 100. It will be appreciated that other suitable connectors may be utilized between the apparatus 100 and the collection syringe 66, such as a luer slip connection. The first end 118 of the barrel 112 may include a female luer 196 (FIG. 4B).

Referring now to FIGS. 5-10, the apparatus 100 may further include a colorimetric assay assembly 200 for detecting free hemoglobin in a fluid sample, such as the fluid sample 32. The colorimetric assay assembly 200 is housed in a colorimetric chamber 211 (FIGS. 5, 10A, and 10D) of the barrel 112. In one non-limiting embodiment, the colorimetric chamber 211 may be formed in part by a portion of an exterior surface of the sidewall 122 of the barrel 112 and a cover 212. The colorimetric chamber 211 is in fluid communication with the internal chamber 126 of the barrel 112 via a passage 210 downstream of the clot catcher 133 and upstream of the liquid-impermeable membrane 149, as shown in FIG. 10. The colorimetric chamber 211 is configured to hold the colorimetric assay assembly 200 so at least a portion of the fluid sample in the internal chamber 126 of the barrel 112 passes into the colorimetric chamber 211 and into contact with the colorimetric assay assembly 200.

Figure 5:
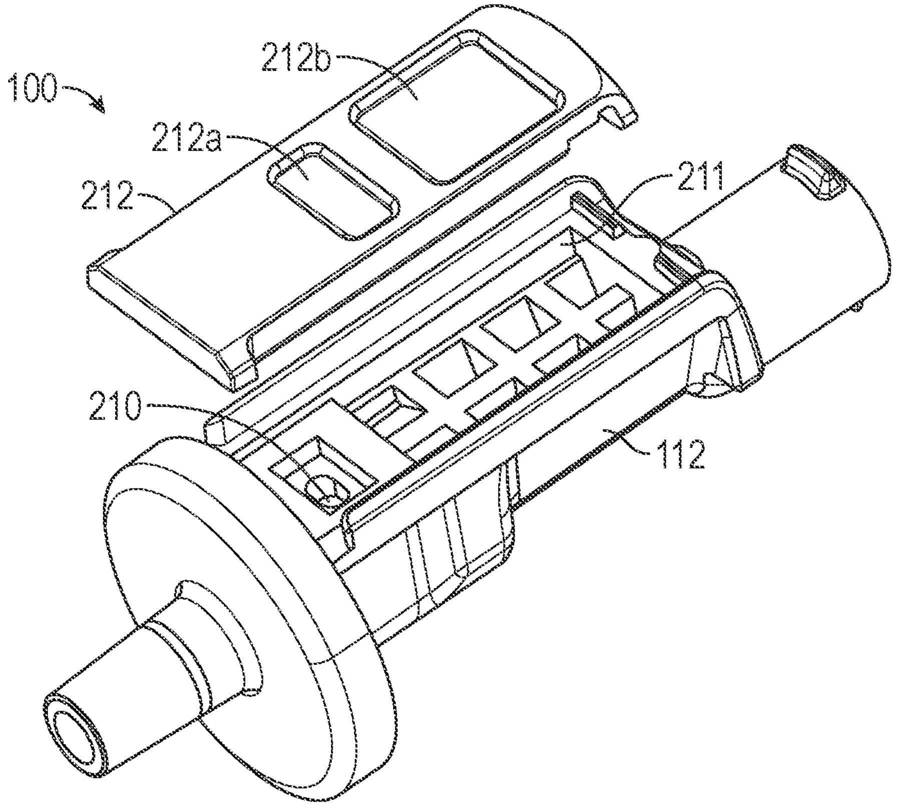
FIG. 5 is a partially exploded, perspective view of the apparatus of FIG. 4A illustrated with a colorimetric assay assembly removed.

The cover 212 may be formed entirely or in part with the same material as that forming the barrel 112. For example, the cover 212 may be formed of any suitable material, such as, without limitation, plastics such as polycarbonate, polystyrene, polyacrylates, and polyurethane, or medical-grade polymers. The cover 212 may be transparent or formed with transparent windows for viewing the colorimetric assay assembly 200. In a manner to be described below, the cover 212 may include a fill pane 212*a* for observing when a sufficient volume of the fluid sample 32 has entered the colorimetric chamber 211 and a read pane 212*b* for assessing the hemolysis level, as shown in FIGS. 5 and 10. In one non-limiting embodiment, the fill pane 212*a* and the read pane 212*b* may be delineated from the remainder of the cover 212 by reducing the thickness of the cover 212 so as to define the fill pane 212*a* and the read pane 212*b*. In another embodiment, the fill pane 212*a* and the read pane 212*b* may be formed of a transparent material that is different from the material used to form the cover 212, such as glass. In another embodiment, the fill pane 212*a* and the read pane 212*b* may be voids or openings through the cover 212.

As shown in FIGS. 6A-10D, the colorimetric assay assembly 200 includes a sample application pad 214 in fluidic contact with a colorimetric detection pad 216. The sample application pad 214 is configured for application of a portion of the fluid sample 32 to the colorimetric assay assembly 200. The sample application pad 214 may receive and absorb (a portion of) the fluid sample 32, and the fluid sample 32 from the internal chamber 126 via the passage 210 may then be absorbed into the colorimetric detection pad 216 from the sample application pad 214.

Figure 6A:
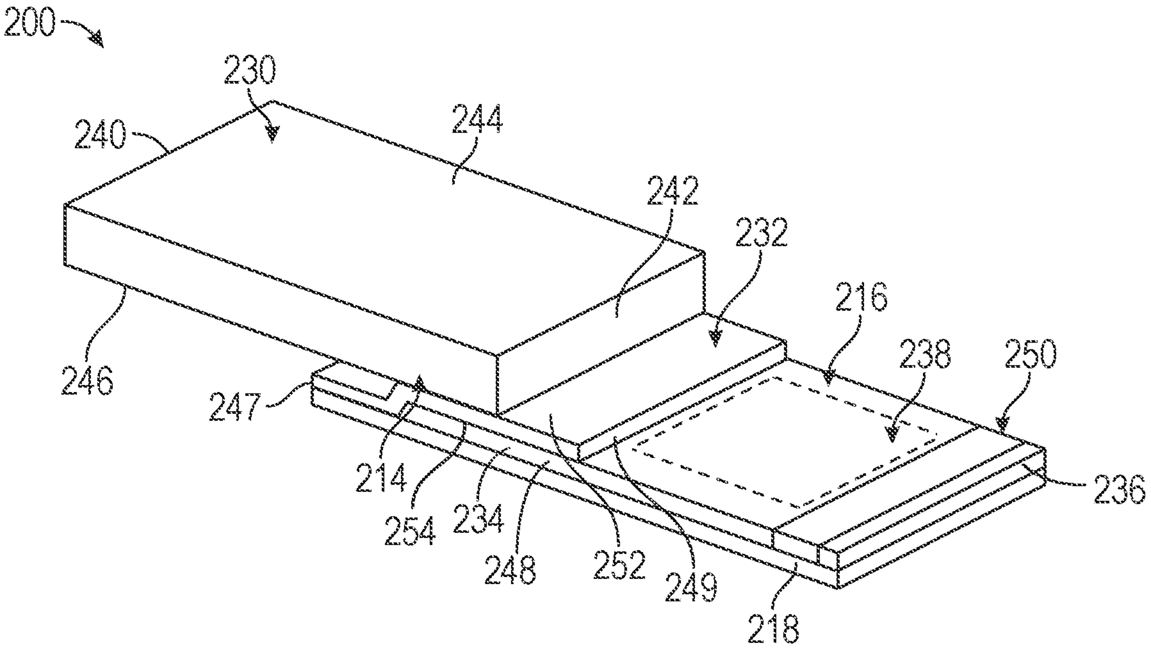
FIG. 6A is a perspective view of a non-limiting embodiment of a colorimetric assay assembly constructed in accordance with the inventive concepts disclosed herein.

Referring to FIG. 6A, the sample application pad 214 may be formed of two layers with different sizes and dimensions and do not fully overlap with one another. The sample application pad 214 includes a prefiltration layer 230 (FIGS. 7A-8H) formed of a prefiltration material, such as a glass fiber material, and a filtration layer 232 formed of a different filtration material, such as an asymmetric polysulfone material.

It is desirable for the fluid sample 32 to flow sequentially through the prefiltration layer 230 and the filtration layer 232. In this regard, the prefiltration layer 230 and the cover 212 are configured so as to direct the fluid sample 32 into and through the prefiltration layer 230 to the filtration layer 232, preferably without permitting the fluid sample 32 to flow around the prefiltration layer 230. This is accomplished by (a) configuring the prefiltration layer 230 to present a hydrophilic receiving surface 246 (described below) towards the fluid sample 32 to receive and enhance absorption of the fluid sample 32, and/or (b) configuring the cover 212 to include a mechanical fluid director (referred to below as a "compression rib 262") to engage a distal surface 244 (opposite the hydrophilic receiving surface 246) to form a seal adjacent to three edges of the prefiltration layer 230 and thereby reduce the possibility of the fluid sample 32 flowing around the prefiltration layer 230. By enhancing absorption of fluid sample 32 by the prefiltration layer 230 and encouraging the fluid sample 32 to flow through, rather than around, the prefiltration layer 230, enhanced prefiltration of the fluid sample 32 is achieved.

The prefiltration layer 230 has a first end 240, a second end 242, a distal surface 244, and a hydrophilic receiving surface 246. The filtration layer 232 has a first end 247, a second end 249, an upper surface 252, and a lower surface 254. At least a portion of the prefiltration layer 230 adjacent to the second end 242 thereof overlaps a portion of the filtration layer 232 between the first end 247 and the second end 249 thereof. The overlapping portions of the prefiltration layer 230 and filtration layer 232 may be attached to one another, or the overlapping portion of the prefiltration layer 230 may simply be layered upon the filtration layer 232, so a portion of the hydrophilic receiving surface 246 of the prefiltration layer 230 is in contact with a portion of the upper surface 252 of the filtration layer 232.

In one embodiment, the prefiltration layer 230 has dimensions of length l, width w, and height h, constrained by the colorimetric chamber 211 and the cover 212. In one embodiment, the width w is about 6 mm, the length l is about 10 mm and the height h is about 1.22 mm. In some embodiments, the height h is within about 0.13 mm of 1.22 mm.

In one embodiment, the prefiltration layer 230 is constructed of a glass fiber prefilter with an acrylic binder. The prefiltration layer 230 may have, for example, a dispersed oil particulate efficiency (DOP efficiency) of >99.97% retention. An exemplary prefiltration layer 230 may be constructed of a glass fiber prefilter such as the Extra Thick Glass Fiber prefilter S80038 (Pall Corporation, New York City, New York). In one embodiment, the binder may be selected based on a desired wetting (attractive) property between the prefiltration layer 230 and the fluid sample 32. For example, the binder may be configured for a desired hydrophilicity or hydrophobicity of portions of the prefiltration layer 230. The wetting property may be measured as a static contact angle in which static contact angles exceeding 90 degrees are considered hydrophobic and static contact angles less than 90 degrees are considered hydrophilic.

The hydrophilic receiving surface 246 of the prefiltration layer 230 is aligned and is in fluid communication with the passage 210 and positioned to receive the fluid sample 32 from the internal chamber 126 of the barrel 112.

Figure 6B:
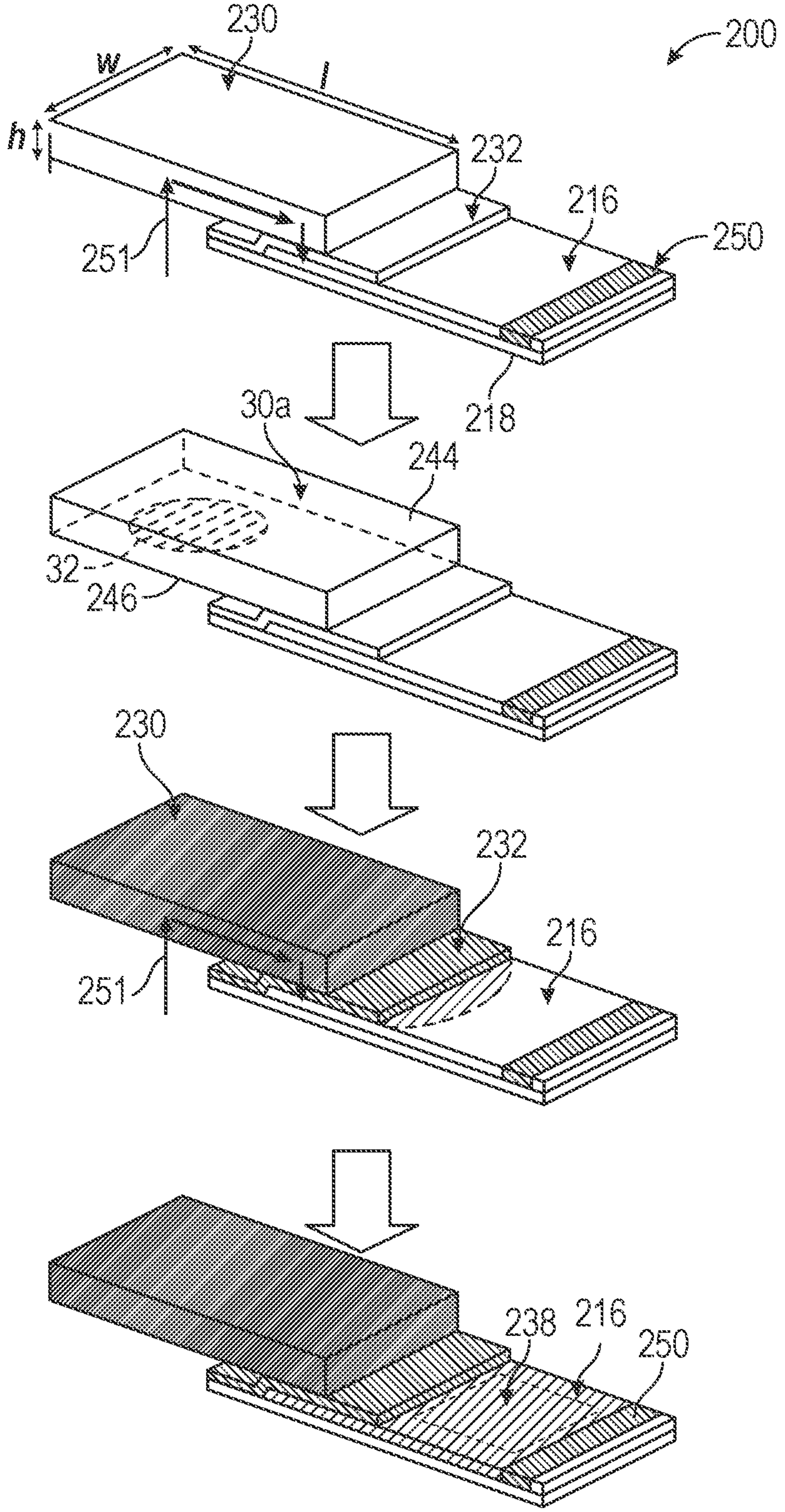
FIG. 6B contains perspective views illustrating a sample blood flow within the colorimetric assay assembly of FIG. 6A.

Generally, when the fluid sample 32 is applied to the hydrophilic receiving surface 246, the fluid sample 32 saturates the prefiltration layer 230. It is desirable to direct the fluid sample 32 along the fluid path 251 (as shown in FIG. 6B) towards the filter layer 232. To that end, various prefiltration layer 230 embodiments described below are configured to direct the fluid sample 32 along the fluid path 251 thereby reducing overflow (e.g., the fluid sample 32 extending beyond the prefiltration layer 230 other than extending towards the filtration layer 232).

Figure 7A:
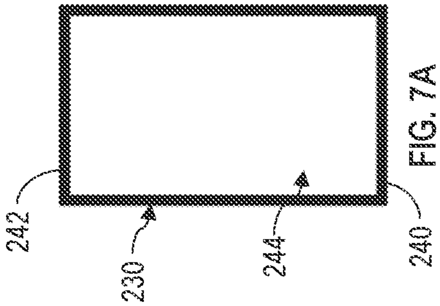
FIG. 7A is a diagram of an exemplary embodiment of a first surface of the first layer of the colorimetric assay assembly of FIG. 6B.
Figure 7B:
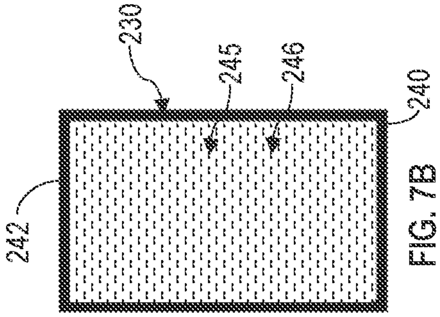
FIG. 7B is a diagram of an exemplary embodiment of a second surface of the first layer of the colorimetric assay assembly of FIG. 6B.

Referring to FIGS. 7A-7B, shown therein are diagrams of exemplary embodiments of the prefiltration layer 230 constructed in accordance with the present disclosure. Shown in FIG. 7A is the distal surface 244 of the prefiltration layer 230 having a first wetting property and shown in FIG. 7B is the hydrophilic receiving surface 246 of the prefiltration layer 230 having a second wetting property as indicated by texture 245 of FIG. 7B. The texture 245 may be, for example, a series of peaks and valleys formed by glass fibers on the hydrophilic receiving surface 246 that cause the hydrophilic receiving surface 246 to have a more rough texture than the distal surface 244. The texture 245 creates an uneven surface which increases surface area on the hydrophilic receiving surface 246 as compared to the distal surface 244, which is smoother or non-texturized (e.g., is absent of a series of peaks and valleys). Increasing the surface area of the hydrophilic receiving surface 246 advantageously allows increased and/or enhanced absorption of fluid sample 32 (e.g., as received via passage 210) by the prefiltration layer 230 thereby encouraging the fluid sample 32 to flow into and through, rather than around, the prefiltration layer 230.

The first wetting property, measured as a static contact angle, of the distal surface 244 is greater than the second wetting property of the hydrophilic receiving surface 246 thereby resulting in the distal surface 244 being less hydrophilic than the hydrophilic receiving surface 246. In some embodiments, the hydrophilic receiving surface 246 is hydrophilic to enhance absorption of the fluid sample 32. An interior of the prefiltration layer 230 and the distal surface 244 may be considered a prefiltration portion with the first wetting property being more hydrophobic (e.g., higher static contact angle) than the second wetting property.

A wetting property, as used herein, may refer to a propensity or tendency of a surface/material to attract or repel water. The wetting property may be hydrophilic, i.e., tending to attract water, or hydrophobic, i.e., tending to repel water. When comparing two or more hydrophobicities of a first component and a second component, a greater, or increased, hydrophobicity of the first component means that the first component has a greater, or stronger/increased, hydrophobic property than the second component. When comparing two wetting properties, the smaller wetting property is more hydrophilic, whereas the larger wetting property is more hydrophobic.

In one embodiment, the distal surface 244 has the first wetting property being more hydrophobic than the second wetting property of the hydrophilic receiving surface 246. One or more hydrophobic or hydrophilic agent may be applied to one or more of the distal surface 244 and the hydrophilic receiving surface 246 to selectively modify the first wetting property and/or the second wetting property, respectively. For example, optionally a hydrophobic agent may be applied to the distal surface 244 to increase the first wetting property. Alternatively, or additionally, a hydrophilic agent may be applied to the hydrophilic receiving surface 246 to decrease the wetting property (i.e., make the hydrophilic receiving surface 246 more hydrophilic as compared to the distal surface 244). The hydrophobic agent may include, for example, carbon, or something carbon like, while the hydrophilic agent may include, for example, a hydrophilic acrylic. The hydrophilic agent selected to apply to the hydrophilic receiving surface 246 should be selected so as to enhance absorption of the sample fluid 32 into the prefiltration layer 230 to help prevent flooding in which the sample fluid 32 flows around the prefiltration layer 230. Accordingly, as used herein, the term hydrophilic with respect to the hydrophilic receiving surface 246 is a comparative term indicating that the hydrophilic receiving surface 246 is more hydrophilic than the distal surface 244.

Fiber density may be used to refer to how close various fibers of the prefiltration layer 230 are to each other. For example, on average, a more highly fiber dense material may have a smaller spacing between adjacent fibers than a less highly fiber dense material.

For example, when the fluid sample 32 is blood comprising plasma, red blood cells, and white blood cells, a spacing between adjacent fibers at the hydrophilic receiving surface 246 may be between 1/10 and 1/2 times the width of a red blood cell to allow the plasma, red and white blood cells to enter the prefiltration layer 230. Above the hydrophilic receiving surface 246, the spacing between adjacent fibers may be the same as or slightly more than the width of the red blood cells and greater than the width of molecules forming the plasma so that the plasma and free hemoglobin indicative of ruptured red blood cells can freely pass through the prefiltration layer 230, but at least some of the red and white blood cells become trapped within the prefiltration layer 230. In some embodiments, the fiber density of the hydrophilic receiving surface 246 and the distal surface 244 are the same. In one embodiment, red blood cells and white blood cells remaining in the sample fluid 32 after passing through the prefiltration layer 230 may then pass through the filtration layer 232 where additional red blood cells and/or white bloods cells may become trapped within the filtration layer 232 such that the plasma and the free hemoglobin remaining in the sample fluid 32 pass to the colorimetric detection pad 216.

The second wetting property of the hydrophilic receiving surface 246 may affect the absorption of the fluid sample 32 into the prefiltration layer 230 such as by increasing the rate of absorption and/or directing the fluid sample 32 into and through the prefiltration layer 230 toward the filtration layer 232 (i.e., along the fluid path 251, as shown in FIG. 6B). The prefiltration layer 230 may have at least two or more different wetting properties either on or within the prefiltration layer 230. The second wetting property is configured so as to allow or increase absorption of the fluid sample 32 into the prefiltration layer 230. The wetting property may vary between the hydrophilic receiving surface 246 and the distal surface 244 of the prefiltration layer 230. Once the fluid sample 32 is absorbed into the prefiltration layer 230, the fibers within the prefiltration layer 230 may filter out one or more predetermined constituents of the fluid sample 32.

Referring to FIGS. 8A-8H, shown therein are diagrams of exemplary embodiments of one or more various fluid pathway 300 constructed in accordance with the present disclosure. Each fluid pathway 300 is formed in at least the hydrophilic receiving surface 246 of the prefiltration layer 230 and extends towards the distal surface 244. Each fluid pathway is operable to increase absorption of the fluid sample 32 into the prefiltration layer 230 and along the fluid path 251 (shown in FIG. 6B). In other words, each fluid pathway 300 is configured to increase the surface area available on the hydrophilic receiving surface 246 such that absorption of the fluid sample 32 is directed, encouraged, and/or enhanced into the prefiltration layer 230 and along the fluid path 251, thereby decreasing or eliminating pooling of the fluid sample 32 around the prefiltration layer 230.

Figure 8A:
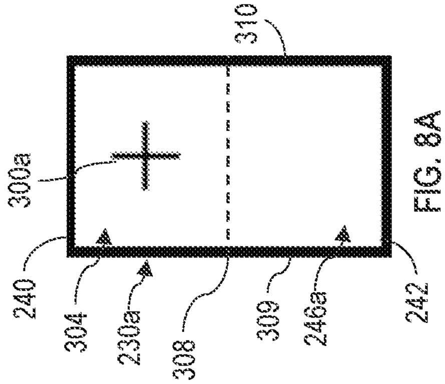
FIGS. 8A-8H are diagrams of exemplary embodiments of the second surface of the first layer of the colorimetric assay assembly comprising various fluid pathway configurations.

In one embodiment, shown in FIG. 8A is a prefiltration layer 230 a having a hydrophilic receiving surface 246*a* and a fluid pathway 300*a* constructed as a void, with a cross-shaped cross-section geometry, formed in the hydrophilic receiving surface 246*a*. In some embodiments, the fluid pathway 300*a* extends from the hydrophilic receiving surface 246*a* but does not extend through the distal surface 244*a*; however, in other embodiments, the fluid pathway 300*a* may further extend through the distal surface 244*a*. In some embodiments, more than one fluid pathway 300*a* may be formed in the hydrophilic receiving surface 246*a*. The fluid pathway 300*a* increases the surface area of the hydrophilic receiving surface 246 to enhance absorption of the fluid sample 32 into the prefiltration layer 230*a*.

In some embodiments, each fluid pathway 300 is positioned in a modification region 304 of the hydrophilic receiving surface 246*a* of the prefiltration layer 230*a*. The modification region 304 is a portion of the hydrophilic receiving surface 246*a* bound by the first end 240 and a boundary 308 and is aligned and is in fluid communication with the passage 210 and positioned to receive the fluid sample 32 from the internal chamber 126 of the barrel 112. The boundary 308 may extend from a third edge 309 of the prefiltration layer 230*a* to a fourth edge 310 of the prefiltration layer 230*a*.

Figure 8B:
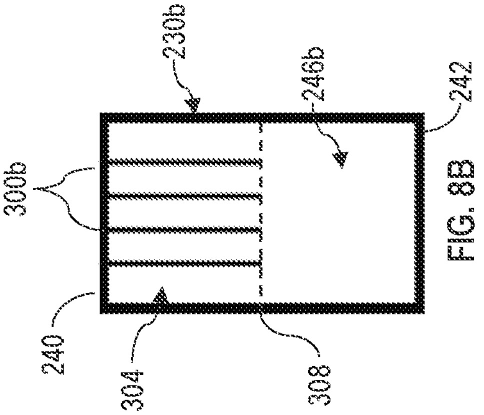

In one embodiment, shown in FIG. 8B is a prefiltration layer 230*b* having a hydrophilic receiving surface 246*b* and a fluid pathway 300*b* as multiple spaced apart slits in the hydrophilic receiving surface 246*b* extending from the first end 240 towards the boundary 308. While the fluid pathway 300*b* is shown as extending from the first end 240 to the boundary 308, in some embodiments the fluid pathway 300*b* may not extend the entire distance from the first end 240 to the boundary 308, i.e., the fluid pathway 300*b* may stop short of reaching the boundary 308. In one embodiment, one or more fluid pathway 300*b* is 4 mm long, and may be between 2 mm long and 10 mm long, and may be disposed from one another by 1.5 mm, or be disposed from one another by between 0.5 mm and 3 mm. In some embodiments, each fluid pathway 300*b* is formed in the prefiltration layer 230*b* with a no-kerf slit such that the slit may be referred to as a kiss-cut.

In some embodiments, the fluid pathway 300*b* extends from the distal surface 244 to the hydrophilic receiving surface 246*a*, bisecting the prefiltration layer 230*b*, however, in other embodiments, the fluid pathway 300*b* does not extend through the distal surface 244. For example, the fluid pathway 300*b* may extend from the hydrophilic receiving surface 246*b* towards the distal surface 244 but may not extend through the distal surface 244.

Figure 8C:
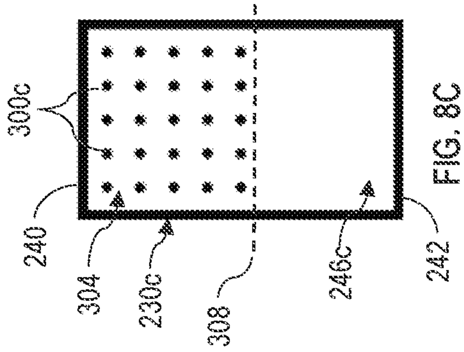

In another embodiment, shown in FIG. 8C, a prefiltration layer 230*c* has a hydrophilic receiving surface 246*c* and a fluid pathway 300*c* constructed as a plurality of perforations 300*c* in the hydrophilic receiving surface 246*c* of the prefiltration layer 230*c*. The plurality of perforations 300*c* are shown as perforations 300*c* having a circular cross-section and extending from the hydrophilic receiving surface 246*c* towards the distal surface 244, and, in some embodiments, may extend through the distal surface 244. As shown in FIG. 8C, the perforations 300*c* are distributed on the hydrophilic receiving surface 246*c* in the modification region 304 extending from the first end 240 to the boundary 308. While shown having 25 perforations 300*c*, in some embodiments, the hydrophilic receiving surface 246*c* may include a fewer or a greater number of perforations 300*c*.

In some embodiments, the perforations 300*c* have a cross-sectional area of about 2 $mm^2$ while in other embodiments, the perforations 300*c* have a cross-sectional area of between 0.5 $mm^2$ and 4 $mm^2$.

Figure 8D:
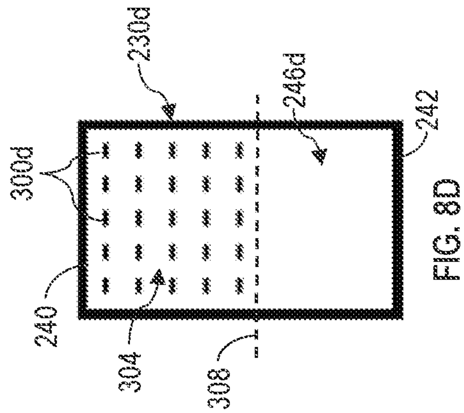

The perforations 300*c* may have a cross-section of any suitable geometry, including, but not limited to circular (as shown in FIG. 8C), oval, square, or rectangular (shown as perforations 300*d* in FIG. 8D).

Figure 8E:
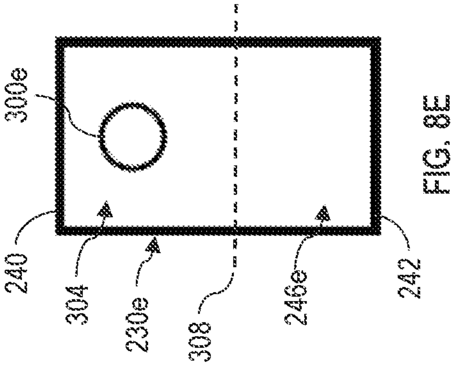

In one embodiment, shown in FIG. 8E, a prefiltration layer 230*e* has a hydrophilic receiving surface 246*e* and a fluid pathway 300*e* in the hydrophilic receiving surface 246*e* of the prefiltration layer 230*e* extending towards the distal surface 244. The fluid pathway 300*e* may be formed to have a cross-sectional geometry of any suitable geometry, including, but not limited to, circular, oval, square, or rectangular, and is shown as having a circular geometry. In one embodiment, the prefiltration layer 230*e* has the fluid pathway 300*e* in the modification region 304.

In some embodiments, the fluid pathway 300*e* has a cross-sectional area of about 0.25 $mm^2$ while in other embodiments, the fluid pathway 300*e* has a cross-sectional area of between 0.0625 $mm^2$ and 1.0 $mm^2$, such as, for example, 0.0625 $mm^2$, 0.125 $mm^2$, 0.25 $mm^2$, 0.375 $mm^2$, 0.5 $mm^2$, 0.625 $mm^2$, 0.75 $mm^2$, 0.875 $mm^2$, and 1 $mm^2$, or any area between any of the foregoing cross-sectional areas.

Figure 8F:
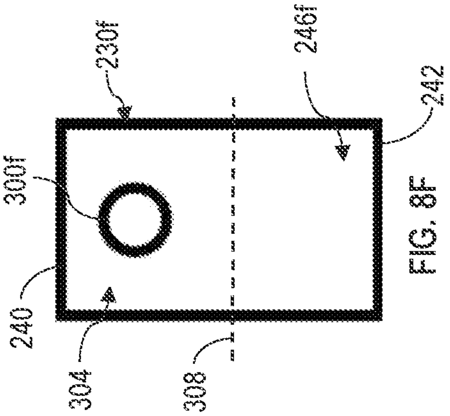
Figure 8H:
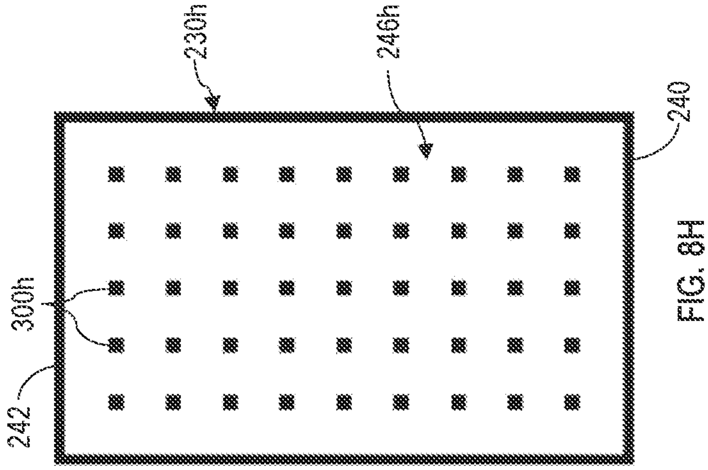

In one embodiment, shown in FIG. 8F, a prefiltration layer 230*f* has a hydrophilic receiving surface 246*f* and a fluid pathway 300*f* in the hydrophilic receiving surface 246*f* of the prefiltration layer 230*f*. The prefiltration layer 230*f* may be constructed similar to the prefiltration layer 230*e* and the fluid pathway 300*f* may be constructed similar to the fluid pathway 300*e*, with the exception that the fluid pathway 300*f* in the prefiltration layer 230*f* extends through the distal surface 244 whereas the fluid pathway 300*e* in the prefiltration layer 230*e* does not extend through the distal surface 244.

Figure 8G:
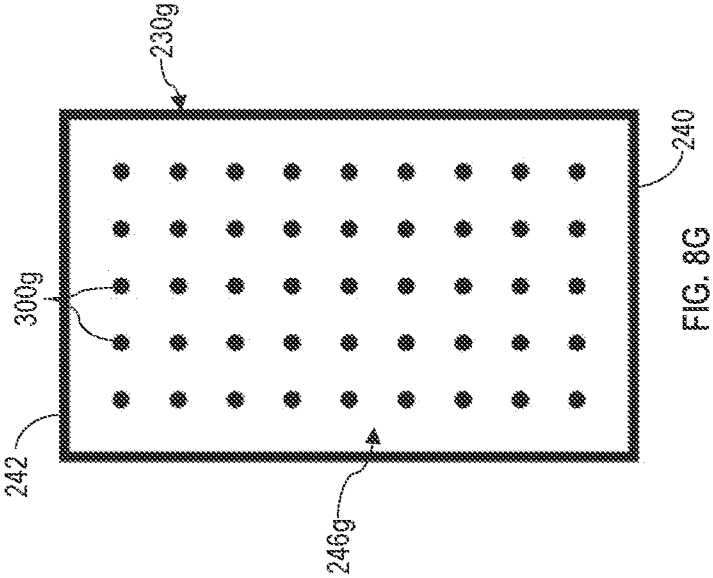

In one embodiment, shown in FIG. 8G, a prefiltration layer 230*g* has a hydrophilic receiving surface 246*g* and a plurality of fluid pathways 300*g* in the hydrophilic receiving surface 246*g* of the prefiltration layer 230*g*. The prefiltration layer 230*g* and the fluid pathways 300*g* may be constructed according to the prefiltration layer 230*c* and the fluid pathways 300*c* described above, with the exception that the plurality of fluid pathways 300*g* are disposed at any location within the hydrophilic receiving surface 246*g* and are not limited to being disposed within the modification region 304 (in FIG. 8C). Similarly, shown in FIG. 8H, a prefiltration layer 230*h* has a hydrophilic receiving surface 246*h* and a plurality of fluid pathways 300*h* in the hydrophilic receiving surface 246*h* of the prefiltration layer 230*h*. The prefiltration layer 230*h* and the fluid pathways 300*h* may be constructed according to the prefiltration layer 230*c* and the fluid pathways 300*c* described above, with the exception that the plurality of fluid pathways 300*h* are disposed at any location within the hydrophilic receiving surface 246*h*, have a square geometry, and are not limited to being disposed within the modification region 304 (in FIG. 8C).

Figure 9:
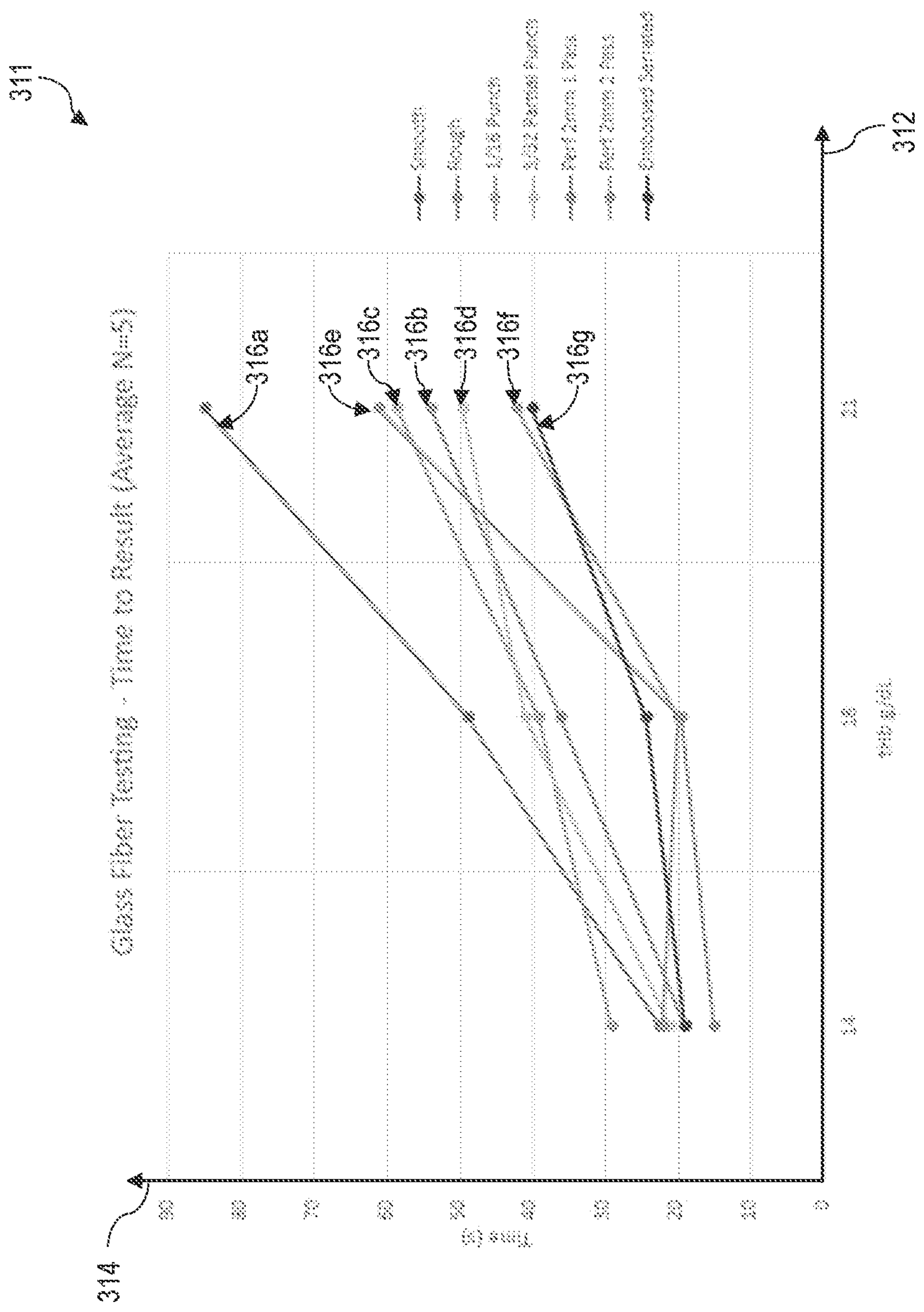
FIG. 9 is a graph of experimental results of an exemplary embodiment of the surface fiber densities of FIGS. 7A-7B and the various fluid pathway configurations of FIGS. 8A-H.

Referring now to FIG. 9, shown therein is an exemplary performance graph 311 showing experimental results of various embodiments of the prefiltration layer 230, such as the prefiltration layer 230*a-h* detailed above. The performance graph 311 is shown with an abscissas axis 312 describing an initial quantity of fluid placed on each prefiltration layer 230 in tHb b/dL, and an ordinate axis 314 showing a time to result 316 for each prefiltration layer 230. The time to result may refer to a time duration starting from when a blood sample is provided to the hydrophilic receiving surface 246 of the prefiltration layer 230 of the sample pad until plasma from the blood sample reaches the control line of the pad. For example, result 316*a* corresponds to the distal surface 244 of the prefiltration layer 230 shown in FIG. 7A, result 316*b* corresponds to the hydrophilic receiving surface 246 of the prefiltration layer 230 shown in FIG. 7B, result 316*c* corresponds to the prefiltration layer 230 having a fluid pathway 300 with a diameter of 1/16 extending from the hydrophilic receiving surface 246 through the distal surface 244, result 316*d* corresponds to the prefiltration layer 230 having a fluid pathway 300 with a diameter of 3/32 extending from the hydrophilic receiving surface 246 towards, but not through, the distal surface 244, result 316*e* corresponds to the prefiltration layer 230 having a first plurality of fluid pathways 300 as perforations with a 2 mm diameter and extending from the hydrophilic receiving surface 246 through the distal surface 244, result 316*f* corresponds to the prefiltration layer 230 having a second plurality (greater than the first plurality) of fluid pathways 300 as perforations with a 2 mm diameter and extending from the hydrophilic receiving surface 246 through the distal surface 244, and result 316*g* corresponds to the prefiltration layer 230 having a plurality of fluid pathways 300 as embossed serrations extending from the hydrophilic receiving surface 246 towards the distal surface 244 but not extending through the distal surface 244.

As shown in the performance graph 311, including one or more fluid pathway 300 in the prefiltration layer 230 and/or lowering the wetting property on the hydrophilic receiving surface 246 relative to the wetting property of the distal surface 244 is generally beneficial as the time to result (as shown on the ordinate axis 314) is generally lower than the higher wetting property (more hydrophobic) and no fluid pathway embodiment of result 316*a*. The lowered time to result indicates an improved flow rate which reduces over-pressurization and reduced leaking around sample application pad 214 (e.g., around the prefiltration layer 230).

Referring back to FIGS. 6A-B, accordingly, the prefiltration layer 230 and the filtration layer 232 of the sample application pad 214 may partially overlap with one another to form an overlapping portion and a non-overlapping portion. In some embodiments, the non-overlapping portion is congruous to the modification region 304. Referring to the workflow shown in FIG. 6B of the colorimetric assay assembly 200, the non-overlapping portion of the prefiltration layer 230 (at the hydrophilic receiving surface 246) may receive and absorb a portion of the fluid sample 32 from the internal chamber 126 via the passage 210 (shown in the second panel of FIG. 6B). The fluid sample 32 may then be absorbed into the colorimetric detection pad 216 from the overlapping portion of the sample application pad 214 (shown in the third and fourths panels of FIG. 6B). In particular, as the fluid sample 32 is absorbed or saturated throughout the prefiltration layer 230 (which may be visible through fill pane 212*a* shown in FIG. 5) along a fluid path 251, the fluid sample 32 may then be filtered or passed through from the overlapping portion of the prefiltration layer 230 (at the hydrophilic receiving surface 246) to the overlapping portion of the filtration layer 232 (at the upper surface 252), as shown in the third panel of FIG. 6B. As the fluid sample 32 is absorbed or saturated throughout the filtration layer 232, the fluid sample 32 may then be filtered or passed through from filtration layer 232 (at the lower surface 254) to a sample application site 248 of the colorimetric detection pad 216 (at a portion of its upper surface that overlaps with the lower surface 254 of the filtration layer 232), as shown in the third and fourth panels of FIG. 6B. The component(s) of the fluid sample 32 (e.g., plasma and free hemoglobin, if any) absorbed by the colorimetric detection pad 216 then flow via capillary action from the sample application site 248 to a control line 250 on the colorimetric detection pad 216 for detection of free hemoglobin within the colorimetric detection pad 216 indicative of hemolysis (shown in the fourth panel).

When the fluid sample 32 is blood, the sample application pad 214 is porous to plasma and free hemoglobin present in the fluid sample 32 but is not porous to red blood cells so red blood cells present in the fluid sample 32 are retained within the prefiltration layer 230 and filtration layer 232 of the sample application pad 214 and are thereby prevented from flowing there through to the colorimetric detection pad 216. Thus, the sample application pad 214 acts as a filter to filter the fluid sample 32 received through the passage 210 such that red blood cells present in the fluid sample 32 (received from the internal chamber 126 via the passage 210) are filtered out and retained within the prefiltration layer 230 and filtration layer 232, while plasma and free hemoglobin present in the fluid sample 32 may pass through the pores of the sample application pad 214 and be received by and absorbed into the colorimetric detection pad 216.

The multi-layered or dual-layered sample application pad 214 advantageously provides improved removal or filtration of red blood cells and detection of hemolysis (via detecting the presence of free hemoglobin on the colorimetric detection pad 216) because, for example, the prefiltration layer 230 of the sample application pad 214 may be capable of retaining at least a portion of the red blood cells and other larger cellular components (without lysing the cells) in the fluid sample 32 and thereby reducing the amount of red blood cells and other larger cellular components that flow into the filtration layer 232 of the sample application pad 214 so as to not overburden filtration occurring at the filtration layer 232.

The colorimetric detection pad 216 defines a path for capillary fluid flow. Components of the fluid sample 32 capable of flowing through the sample application pad 214 then flow through the colorimetric detection pad 216 by capillary action (which may also be referred to as capillary flow). The colorimetric detection pad 216 has a first end portion 234 and a second end portion 236. When the fluid sample 32 is blood, the colorimetric detection pad 216 may be made of any suitable material that allows plasma and free hemoglobin from the fluid sample 32 to freely flow therethrough by capillary action. As one non-limiting example, the colorimetric detection pad 216 may be a nitrocellulose membrane. The colorimetric detection pad 216 may have pores through which certain components of the fluid sample 32 moves by capillary action. The majority of the pores of the colorimetric detection pad 216 may all be substantially the same size or fall within a range of values.

Referring to FIG. 6A, the first end portion of the colorimetric detection pad 216 is in fluidic contact with the lower surface 254 of the filtration layer 232 of the sample application pad 214 and forms a sample application site 248 on the colorimetric detection pad 216. As shown in FIGS. 6A-6B, the colorimetric detection pad 216 also has a read portion 238 and a control line 250 spaced apart from (and, in certain non-limiting embodiments, downstream of) the first end portion 234, sample application site 248, and the read portion 238, with the control line 250 being disposed between the read portion 238 and the second end portion 236 or substantially adjacent to or closer to the second end portion 236 than the first end portion 234.

The sample application pad 214 only covers a portion of the colorimetric detection pad 216 adjacent the first end portion 234 and the sample application site 248 thereof, but not the read portion 238 or the control line 250 thereof; in this manner, at least the read portion 238 of the colorimetric detection pad 216, and the flow of the fluid sample 32 through the colorimetric detection pad 216 into the control line 250 thereof, may be visible via the read pane 212*b* of the cover 212 (as shown in FIGS. 5 and 10A-D).

Referring to FIG. 6A, the colorimetric assay assembly 200 may further include a backing material 218 to which a lower surface of the colorimetric detection pad 216 is attached or otherwise associated (such as, but not limited to, via double stick adhesive).

When a fluid sample 32 (such as, but not limited to, a whole blood sample, urine, or other red blood cell-containing liquid sample) is applied to the colorimetric assay assembly 200, free hemoglobin flows through the sample application pad 214 into the colorimetric detection pad 216, and then from the sample application site 248 of the colorimetric detection pad 216 towards the second end portion 236 and into read portion 238 and the control line 250 thereof. The colorimetric detection pad 216 may be formed of a material that is white in color, thus allowing for a visual read or detection of free hemoglobin via color change of the colorimetric detection pad 216 at the read portion 238 via the read pane 212*b* of the cover 212. For example, if the control line 250 is constructed as a pH indicator line, the control line 250 may be used to detect when the plasma has flowed through the read portion 238 to reach the control line 250 and that the test has completed and is ready for assessment, for example, by using a reference device 360 as described below in relation to FIG. 11. It should be understood that the read portion 238 of the colorimetric detection pad 216 may be defined as a portion of the colorimetric detection pad 216 visible through the read pane 212*b* of the cover 212.

In another embodiment, the control line 250 may be constructed as a hemolysis indicator line with a striped chemical operable to, for example, change color based on a presence of free hemoglobin, e.g., a chemical that reacts to free hemoglobin. Alternatively, the control line 250 may be present in the colorimetric detection pad 216, and the colorimetric detection pad 216 may further include the hemolysis indicator line in addition to the control line 250.

While one particular, non-limiting embodiment of the colorimetric assay assembly 200 is shown in FIGS. 6A and 6B, it will be understood that the design and configuration of the colorimetric assay assembly 200 shown is for purposes of example only. The scope of the present disclosure includes adapting the design and configuration of the colorimetric assay assemblies of the present disclosure, so long as the colorimetric assay assembly remains capable of functioning in accordance with the present disclosure.

For example (but not by way of limitation), it will be understood that the prefiltration layer 230 (of prefiltration material) and the filtration layer 232 (of asymmetric polysulfone material) of the sample application pad 214 need not be symmetrical with one another (i.e., they can differ from one another in size, length, width, and/or thickness). In addition, the prefiltration layer 230 and filtration layer 232 of the sample application pad 214 need not be congruous with one another, and therefore each layer can have an area that does not overlap with the other layer. The only requirement is that at least a portion of the prefiltration layer 230 must overlap a sufficient portion of the filtration layer 232 so the fluid sample 32 can flow through the prefiltration layer 230 into the filtration layer 232 and then flow from the filtration layer 232 into the sample application site 248 of the colorimetric detection pad 216.

In use, the collection syringe 66 is interlockingly engaged with the apparatus 100 and both are positioned in an upright orientation with the apparatus 100 above the collection syringe 66. When the apparatus 100 includes no filter member 16, a user may remove bubbles from the fluid sample in a conventional manner discussed above. The plunger 80 of the collection syringe 66 is displaced axially along the reservoir 82 a distance from the rear end 78 towards the front end 76 of the syringe body 74. Movement of the plunger 80 within the reservoir 82 causes at least a portion of the fluid sample to be expelled from the reservoir 82 and into the internal chamber 126 of the apparatus 100 via the inlet opening 128 and through the clot catcher 133. Any gas portion of the fluid sample passes through the gas-permeable, liquid-impermeable membrane 149.

A portion of the fluid sample 32 passes into the colorimetric chamber 211 via the passage 210 and into contact with the sample application pad 214. FIG. 6B illustrates a sample blood flow within the colorimetric assay assembly 200. The fluid sample 32 (e.g., blood sample) is applied to the hydrophilic receiving surface 246 of the prefiltration layer 230 of the sample application pad 214 and enters the prefiltration layer 230, as shown in the second panel of FIG. 6B. The fluid sample 32 saturates the prefiltration layer 230 and flows through the overlapping portion into the filtration layer 232 (FIG. 6B, third panel). Saturation of the prefiltration layer 230 may be determined by viewing the prefiltration layer 230 through the fill pane 212*a* of the cover 212, which is aligned with at least a portion of the sample application pad 214.

When the prefiltration layer 230 is saturated, plasma and free hemoglobin (if any) from the fluid sample 32 then passes through the filtration layer 232 and enters the colorimetric detection pad 216 and flows from the sample application site 248 towards the second end portion 236 and into read portion 238 and then to the control line 250 thereof (fourth panel). In one non-limiting embodiment, the plasma that reaches the control line 250 turns the control line 250 from a yellow color to a blue color, indicating that the read portion 238 of the colorimetric detection pad 216 of the colorimetric assay assembly 200 is ready to be read through the read pane 212*b*, which is aligned with the read portion 238 and the control line 250.

Figure 10A:
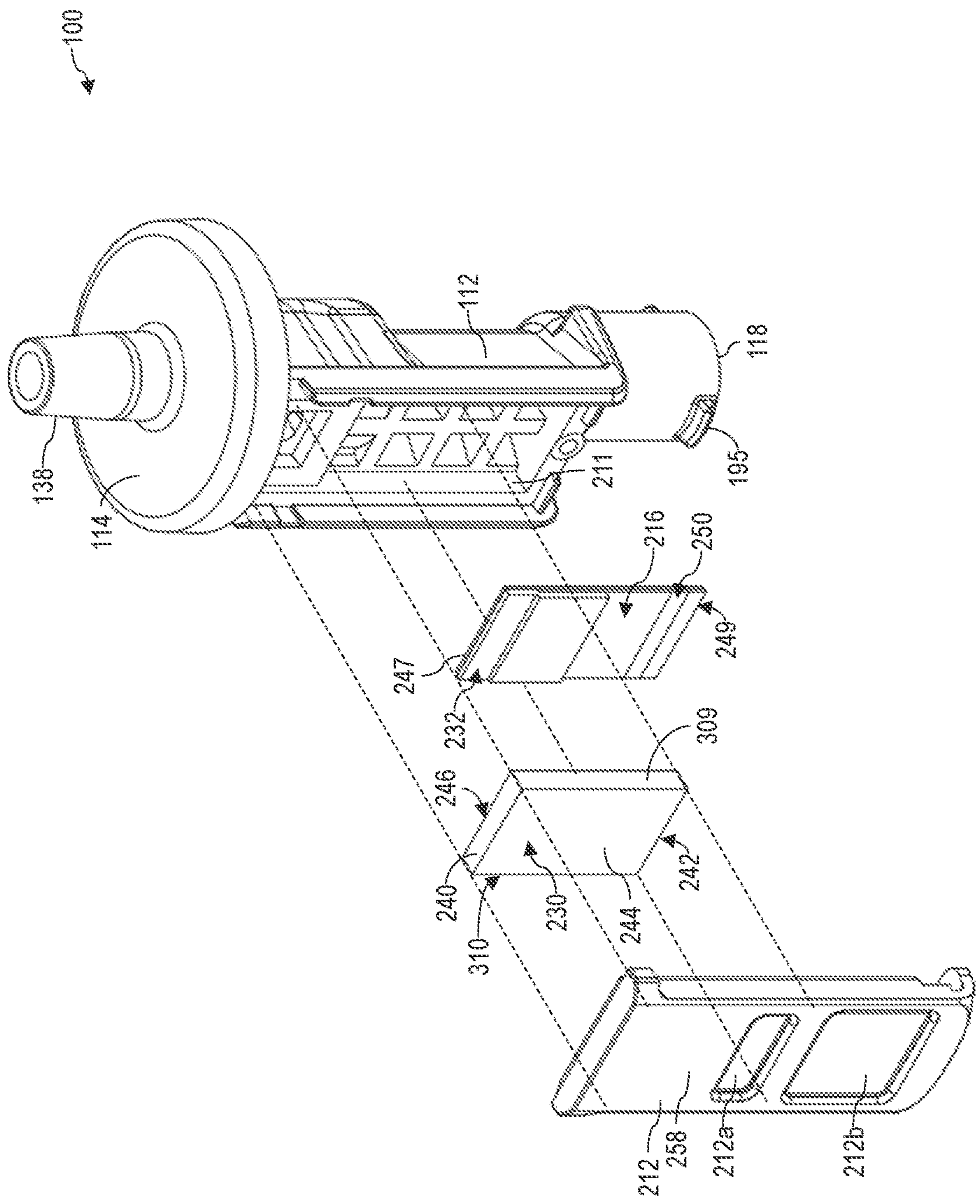
FIG. 10A is a perspective exploded view of another exemplary embodiment of the apparatus constructed in accordance with the present disclosure.

Referring now to FIG. 10A, shown therein is a perspective exploded view of an exemplary embodiment of the apparatus 100 constructed in accordance with the present disclosure. Shown in FIG. 10A, the prefiltration layer 230 and the filtration layer 232 of the sample application pad 214 are disposed between the cover 212 and the colorimetric chamber 211. In this manner, the colorimetric chamber 211 holds the colorimetric assay assembly 200 so at least a portion of the fluid sample in the internal chamber 126 of the barrel 112 passes into the colorimetric chamber 211 and into contact with the hydrophilic receiving surface 246 of the prefiltration layer 230 of the colorimetric assay assembly 200.

Figure 10C:
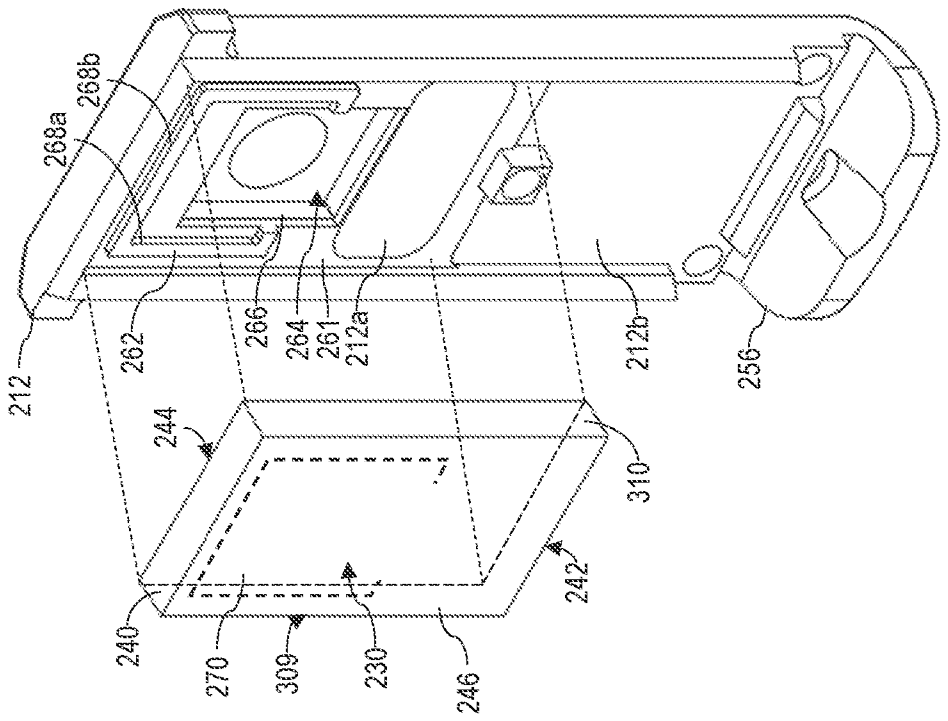
FIG. 10C is an exploded perspective view of an exemplary embodiment of the cover and the first layer constructed in accordance with the present disclosure.
Figure 10B:
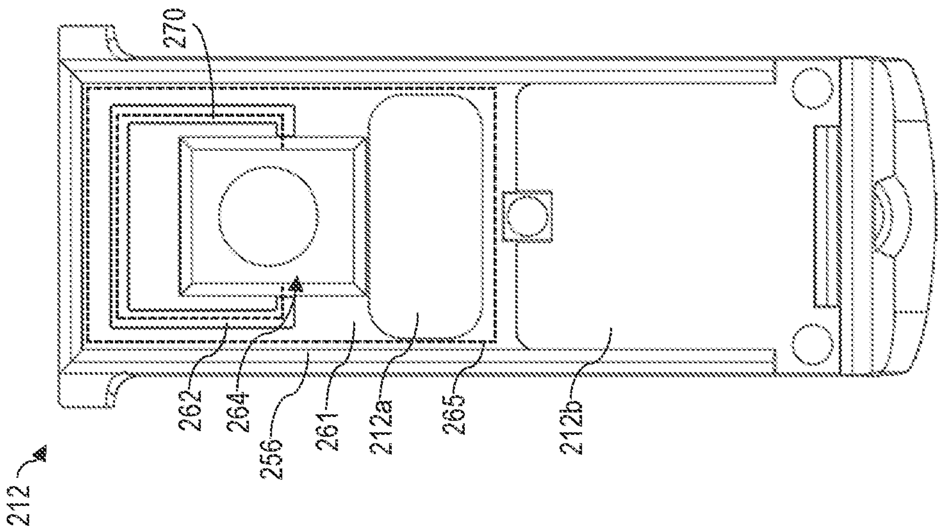
FIG. 10B is an inside-facing view of an exemplary embodiment of the cover constructed in accordance with the present disclosure.
Figure 10D:
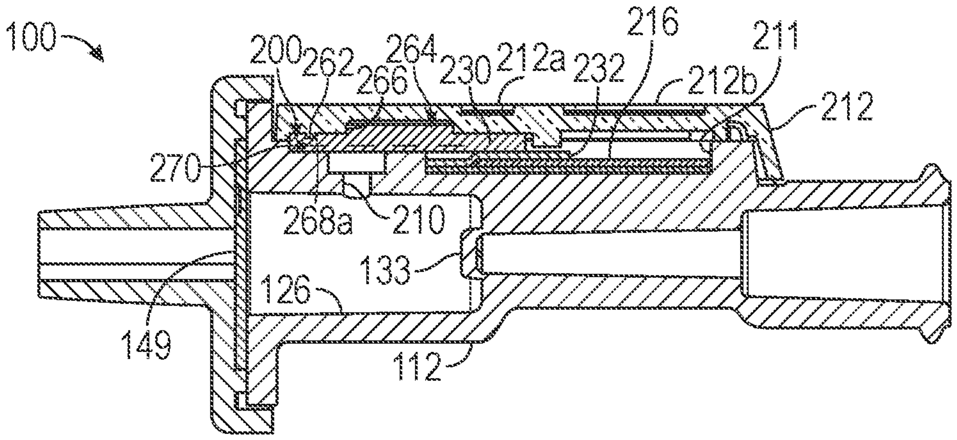
FIG. 10D is a cross-sectional view taken along line 10D-10D of FIG. 4A.

Referring now to FIG. 10B, shown therein is an inside-facing view of an exemplary embodiment of the cover 212 constructed in accordance with the present disclosure. The cover 212 further includes a housing 256 having an outside surface 258 (see FIG. 10A), an inside surface 261 and configured to form at least a compression rib 262 and a debossed cavity 264. Further shown in FIG. 10B is an outline 265 indicating how the prefiltration layer 230 is disposed against the cover 212. The compression rib 262 may be provided with a U-shape in which an area is bounded on multiple sides, i.e., three-four sides by the compression rib 262, as shown in FIG. 10B. At least a portion of the debossed cavity 264 is positioned within the area bounded by the compression rib 262. The colorimetric chamber 211 can be formed between a recessed surface within the barrel 112, and the inside surface 261 of the housing 256 of the cover 212. As indicated by the outline 265, when the prefiltration layer 230 is positioned within the colorimetric chamber, the compression rib 262 engages and compresses a portion of the prefiltration layer 230 to direct the fluid sample 32 towards the filtration layer 232. In the embodiment shown, the debossed cavity 264 overlaps the area bounded by the compression rib 262, and extends away from the compression rib 262 such that the debossed cavity 264 extends towards the cover 212 while the compression rib 262 protrudes away from the cover 212 toward the colorimetric chamber 211. In one embodiment, the debossed cavity 264 is at least partially disposed between the compression rib 262 and the fill pane 212*a*.

Referring now to FIG. 10C, shown therein is an exploded perspective view of an exemplary embodiment of the cover 212 and the prefiltration layer 230 constructed in accordance with the present disclosure. As shown in FIG. 10C, the debossed cavity 264 is defined by the inside surface 261 forming a wall 266 and extending towards the outside surface 258 (shown in FIG. 10A). The compression rib 262 may be formed from the housing 256 and may extend away from the outside surface 258 thereby forming an interior rib wall 268*a* and an exterior rib wall 268*b*.

In this manner, when the apparatus 100 is assembled (as shown in the perspective exploded view of FIG. 10A and shown as a cross-sectional diagram in FIG. 10D), the compression rib 262 engages and compresses at least a portion of the prefiltration layer 230 of the sample application pad 214 in order to modify a flow path of the fluid sample 32 in the prefiltration layer 230 to be along the fluid path 251. In one embodiment, the compression rib 262 directs the flow path of the fluid sample 32 to transfer the fluid sample 32 through the prefiltration layer 230 along the fluid path 251 (FIG. 6B), thereby advantageously reducing flooding and/or streaking. The compression rib 262 directs the fluid sample 32 away from the first end 240, the third edge 309 and the fourth edge 310 towards the second end 242.

More specifically, the compression rib 262 presses against the distal surface 244 of the prefiltration layer 230, preferably in an area of the prefiltration layer 230 that does not overlap with the filtration layer 232. By pressing against the distal surface 244 of the prefiltration layer 230, the compression rib 262 forms a zone of variable compression 270 offset from the first end 240, the third edge 309 and the fourth edge 310 within the prefiltration layer 230. When passing the sample fluid 32 through the prefiltration layer 230, the prefiltration layer 230 extends into the debossed cavity 264.

Generally, the zone of variable compression 270 may allow the fluid sample 32 entering the colorimetric chamber 211 to flow within the debossed cavity 264 and to flow within the zone of variable compression 270 thereby directing the fluid sample 32 from the debossed cavity 264 through the prefiltration layer 230 and past the fill pane 212*a*. The fluid sample 32 may then continue through to the filtration layer 232 where any remaining red blood cells in the fluid sample 32 are filtered before the plasma passes through the read portion 238 and reaches the control line 250 of the colorimetric detection pad 216 as described in more detail herein. In one embodiment, the zone of variable compression 270 may be a central region of the prefiltration layer 230 that is disposed away from the first end 240, the third edge 309 and the fourth edge 310 and bounded by the compression rib 262, that is, the compression rib 262 does not come into contact with and/or directly compress the central region. The compression rib 262 indirectly compresses the central region of the prefiltration layer 230, but to a lesser extent than portions of the prefiltration layer 230 contacting the compression rib 262.

Figure 11:
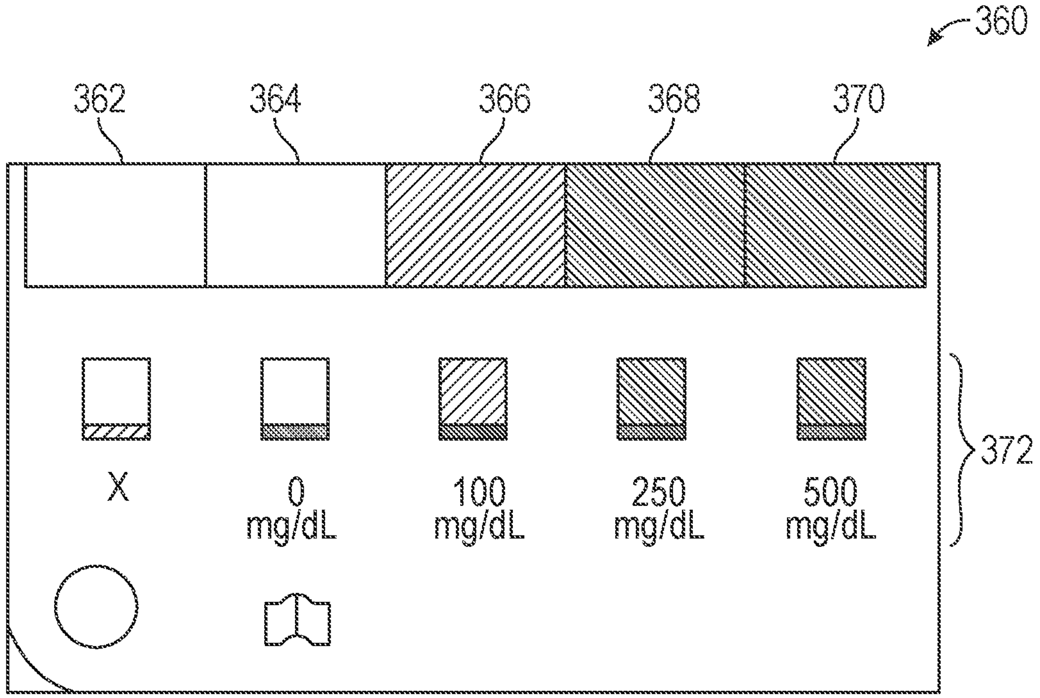
FIG. 11 schematically depicts one non-limiting embodiment of a reference device utilized with the colorimetric assay assembly constructed in accordance with the present disclosure.

FIG. 11 illustrates one non-limiting embodiment of a reference device 360 that can be utilized with the colorimetric assay assembly 200 to visually determine the level of free hemoglobin in the fluid sample 32. The reference device 360 contains a plurality of reference colors, such as, but not limited to, the reference colors 362, 364, 366, 368, and 370, with color 362 having the white/default color of the read portion 238 of the colorimetric detection pad 216 and serving as a negative control, and colors 364, 366, 368, and 370 being various shades of pink/red in increasing intensities/hues, wherein the darker intensities/hues correlate to higher amounts of free hemoglobin/higher degrees of hemolysis. It should be understood that five reference colors are shown for purposes of illustration only. In addition, the reference device 360 also contains a key 372 that correlates each of the reference colors 362, 364, 366, 368, and 370 to a specific concentration of free hemoglobin. That is (and for purposes of example only), the reference color 362 of the key 372 is the negative control (e.g., a color of the read portion 238 of the colorimetric detection pad 216 having not received any portion of the fluid sample 32), while the color 364 indicates that 0 mg/dl of free hemoglobin is present, the color 366 indicates that 100 mg/dl of free hemoglobin is present, the color 368 indicates that 250 mg/dL of free hemoglobin is present, and the color 370 indicates that 500 mg/dL of free hemoglobin is present. In this manner, an individual can determine range of free hemoglobin in the fluid sample 32 in any setting (including, but not limited to, point-of-care or in-home settings) by comparing the color of the read portion 238 of the colorimetric detection pad 216 to the reference colors 364-370 of the reference device 360.

The design and configuration of the reference device 360 of FIG. 11 is shown for purposes of example only; it will be understood that the reference device 360 may be provided with less than five reference colors or more than five reference colors thereon (such as, but not limited to, two, three, four, five, six, seven, eight, nine, ten, or more reference colors thereon). In addition, the shapes and placement of the reference colors may be different. Also, the key 372 may be provided with different shapes/placement that differs from that shown in FIG. 11. The design and configuration of each of the components of the reference device 360 (such as, but not limited to, the reference colors and the key 372) may easily be adapted by a person of ordinary skill in the art to possess any design and configuration that will allow the reference device 360 to function in accordance with the present disclosure. Alternatively, a medical diagnostics device may be utilized to optically detect an amount of free hemoglobin in a fluid sample, such as optically detecting the amount of free hemoglobin (or a level of hemolysis) through the read pane 212*b*, where the medical diagnostics device includes an optical sensor, a processor, and a light source directed at the read portion 238 of the colorimetric detection pad 216 (or, to detect the level of hemoylsis, directed at the control line 250 when the control line 250 is constructed as the hemolysis indicator line described above). The medical diagnostics device may be the liquid sample analyzer 68 or a different device.

A method of optically testing the fluid sample 32 for free hemoglobin/hemolysis may include measuring the characteristics of the light reflected by the read portion 238 and/or the control line 250 of the colorimetric detection pad 216 of the colorimetric assay assembly 200, as described above, after a portion of the fluid sample 32 has been applied to the sample application pad 214 and free hemoglobin has flowed through the sample application pad 214 and into the colorimetric detection pad 216 from the sample application site 248 to the control line 250. The measured amount(s) of, for example, red, orange, green, and/or blue light can then be used in determining the level of free hemoglobin by, for example, comparing the measured amount(s) against one or more reference values.

In exemplary embodiments, the method of testing the fluid sample 32 for free hemoglobin/hemolysis may be performed optically by a medical diagnostic device (not shown) or visually by a medical provider. A medical provider may, for example, visually compare the completed colorimetric assay assembly 200 against a reference device (such as, but not limited to, the reference device 360 shown in FIG. 11), wherein the reference device contains a plurality of reference colors which each correspond to a different level of free hemoglobin/hemolysis, to visually determine the free hemoglobin/hemolysis of the fluid sample 32.

This method may detect the levels of hemoglobin that exceed a predetermined interference value (for example, a manufacturers' interference level). If the sample is above the interference value, the sample would be flagged to inform the end user (i.e., the relevant healthcare provider) that the sample is hemolyzed and therefore compromised.

If the level of free hemoglobin/hemolysis determined in the fluid sample 32 (by visual and/or optical detection of free hemoglobin levels, discussed above) is below a predetermined threshold, then the fluid sample 32 may be considered "uncompromised" and may be subject to further testing. For the uncompromised sample to undergo further testing, the apparatus 100 may be engaged with a testing instrument, such as the liquid sample analyzer 68, with the collection syringe 66 engaged with the apparatus 100. The sample probe 72 (FIG. 2B) of the liquid sample analyzer 68 may then be extended from the sample input port 70 and passed through the gas-permeable, liquid-impermeable membrane 149 to withdraw the liquid portion of the fluid sample 32 from the internal chamber 126 in a "hands free" manner without a user holding the collection syringe 66 or the apparatus 100.

After initial insertion of the apparatus 100 into the sample input port 70 by a user, no additional support is required as the fluid sample 32 is drawn into the liquid sample analyzer 68. The connections between the collection syringe 66, the apparatus 100, and the liquid sample analyzer 68 are sufficiently rigid to prevent gravity from tilting down or putting undue stress on the combination of the connected elements such that a hands-free operation can be performed without additional supporting structures to hold the connected elements together in proper alignment. Similar to that illustrated in FIG. 2B in reference to the apparatus 10, the connections between the collection syringe 66, the apparatus 100, and the liquid sample analyzer 68 are sufficiently rigid to support the collection syringe 66 and the apparatus 100 in an axially aligned relationship with the sample probe 72 of the liquid sample analyzer 68. As such, the user need not remain at the liquid sample analyzer 68 and need not hold the apparatus 100 and/or the collection syringe 66 while a fluid sample in the apparatus 100 is drawn into the liquid sample analyzer 68 via the sample probe 72.

From the above description, it is clear that the inventive concept(s) disclosed herein is well adapted to carry out the objects and to attain the advantages mentioned herein as well as those inherent in the inventive concept disclosed herein. While exemplary embodiments of the inventive concept disclosed herein have been described for purposes of this disclosure, it will be understood that numerous changes may be made which will readily suggest themselves to those skilled in the art and which are accomplished without departing from the scope of the inventive concept disclosed herein and defined by the appended claims.

The following is a list of non-limiting illustrative embodiments of the inventive concepts disclosed herein:

Illustrative embodiment 1. An apparatus, comprising:

a barrel having a first end, a second end opposite the first end, a sidewall extending between the first end and the second end, and an inner surface defining an internal chamber, the sidewall defining at least a portion of a colorimetric chamber in fluid communication with the internal chamber via a passage through the sidewall of the barrel; and a colorimetric assay assembly housed in the colorimetric chamber configured to detect presence of free hemoglobin in a fluid sample, the colorimetric assay assembly comprising:

a sample application pad configured to receive the fluid sample from the internal chamber, wherein the sample application pad is formed of a prefiltration layer of a prefiltration material and a filtration layer of a filtration material, wherein the prefiltration layer comprises a distal surface having a first wetting property and a hydrophilic receiving surface having a second wetting property less than the first wetting property, the hydrophilic receiving surface configured to receive the fluid sample and convey at least a portion of the fluid sample to the filtration layer, the filtration layer being porous to plasma and the free hemoglobin and not porous to red blood cells; and a colorimetric detection pad in fluidic contact with the sample application pad, the colorimetric detection pad being configured to visualize a change of color due to a presence of the free hemoglobin.

Illustrative embodiment 2. The apparatus of Illustrative embodiment 1, wherein the colorimetric chamber is defined by a portion of the sidewall of the barrel and a cover, the cover comprising a housing having an outside surface, an inside surface, and a compression rib extending from the inside surface away from the outside surface, the cover further having a fill pane aligned with the sample application pad for viewing flow of the fluid sample through the sample application pad, and a read pane aligned with the colorimetric detection pad for viewing a read portion and a control line.

Illustrative embodiment 3. The apparatus of any one of Illustrative embodiments 1-2, further comprising a cavity defined by the inside surface and a wall extending towards the outside surface, the cavity disposed against at least a portion of the compression rib and within a fluid path bound by the compression rib.

Illustrative embodiment 4. The apparatus of any one of Illustrative embodiments 1-3, wherein the cavity is at least partially disposed between the compression rib and the fill pane.

Illustrative embodiment 5. The apparatus of any one of Illustrative embodiments 1-4, wherein the prefiltration layer has one or more edges, and wherein the compression rib engages the prefiltration layer of prefiltration material to compress the prefiltration layer to direct the fluid sample away from the one or more edges of the prefiltration layer when the fluid sample moves within the prefiltration layer.

Illustrative embodiment 6. The apparatus of any one of Illustrative embodiments 1-5, wherein the prefiltration layer has a central region, and wherein the compression rib engages the prefiltration layer to direct the fluid sample toward the central region of the prefiltration layer.

Illustrative embodiment 7. The apparatus of any one of Illustrative embodiments 1-6, wherein the filtration material is an asymmetric polysulfone material.

Illustrative embodiment 8. The apparatus of any one of Illustrative embodiments 1-7, wherein the prefiltration material is formed of a glass fiber material having a dispersed oil particulate efficiency of >99.97% retention.

Illustrative embodiment 9. The apparatus of any one of Illustrative embodiments 1-8, wherein the hydrophilic receiving surface of the prefiltration layer further comprises one or more fluid pathway disposed in the hydrophilic receiving surface, each fluid pathway extending from the hydrophilic receiving surface towards the distal surface.

Illustrative embodiment 10. The apparatus of any one of Illustrative embodiments 1-9, wherein at least one of the one or more fluid pathway is a perforation extending from the hydrophilic receiving surface through the prefiltration layer toward the distal surface.

Illustrative embodiment 11. The apparatus of any one of Illustrative embodiments 1-10, wherein the hydrophilic receiving surface of the prefiltration layer further comprises a first edge, a second edge, a third edge, a fourth edge and a boundary extending from the third edge to the fourth edge thereby forming a modification region on the hydrophilic receiving surface and bound by the first edge, the boundary, the third edge, and the fourth edge, and wherein each fluid pathway is disposed within the modification region.

Illustrative embodiment 12. The apparatus of any one of Illustrative embodiments 1-11, wherein at least one of the one or more fluid pathway is a perforation extending from the hydrophilic receiving surface through the prefiltration layer toward the distal surface and wherein each perforation is disposed within the modification region.

Illustrative embodiment 13. The apparatus of any one of Illustrative embodiments 1-12, wherein the one or more fluid pathway further extends from the first edge to the boundary within the modification region.

Illustrative embodiment 14. The apparatus of any one of Illustrative embodiments 1-13, wherein the one or more fluid pathway extends parallel to the third edge and the second edge within the modification region.

Illustrative embodiment 15. The apparatus of any one of Illustrative embodiments 1-14, wherein the one or more fluid pathway is evenly distributed within the modification region.

Illustrative embodiment 16. The apparatus of any one of Illustrative embodiments 1-15, wherein the one or more fluid pathway has one or more of a square, circular, rectangular, or cross-shaped cross-section geometry.

Illustrative embodiment 17. The apparatus of any one of Illustrative embodiments 1-16, wherein at least one of the one or more fluid pathway has a cross-sectional area of about 1 $mm^2$.

Illustrative embodiment 18. The apparatus of any one of Illustrative embodiments 1-17, wherein each of the one or more fluid pathway is a void extending from the hydrophilic receiving surface towards the distal surface and not through the distal surface.

Illustrative embodiment 19. A kit, comprising:

the apparatus of any one of Illustrative embodiments 1-18; and a reference device containing a plurality of reference colors, wherein each reference color corresponds to a different level of free hemoglobin.

Illustrative embodiment 20. A method comprising:

transferring at least a portion of a fluid sample from a fluid sample collection apparatus to an internal chamber of a barrel via an inlet opening;

passing the portion of the fluid sample from the internal chamber of the barrel to a colorimetric chamber and a colorimetric assay assembly housed in the colorimetric chamber, the colorimetric chamber being in fluid communication with the internal chamber, and the colorimetric assay assembly having a sample application pad and a colorimetric detection pad, the sample application pad is formed of a prefiltration layer comprising a prefiltration material having a hydrophilic receiving surface and a distal surface, the hydrophilic receiving surface having a first wetting property configured to receive the fluid sample from the internal chamber, and the distal surface having a second wetting property being less hydrophilic than the first wetting property, the sample application pad is further formed of a filtration layer comprising a filtration material in fluid communication with the prefiltration layer, the hydrophilic receiving surface being configured to pass plasma, red blood cells, white blood cells, and free hemoglobin;

retaining at least red blood cells from the portion of the fluid sample passing into the colorimetric assay assembly in at least one of the filtration layer and the prefiltration layer of the sample application pad;

indicating, by the colorimetric detection pad of the colorimetric assay assembly, a presence of free hemoglobin in the fluid sample; and transferring the fluid sample from the internal chamber to a liquid sample analyzer with a sample probe responsive to the indication of the presence of free hemoglobin in the fluid sample being below a predetermined threshold.

Illustrative embodiment 21. The method of Illustrative embodiment 20, wherein indicating the presence of free hemoglobin further comprises:

applying the portion of the fluid sample to the sample application pad of the colorimetric assay assembly and allowing plasma and the free hemoglobin present in the fluid sample to flow through the hydrophilic receiving surface of the prefiltration layer of the sample application pad towards the colorimetric detection pad while retaining at least some red blood cells present in the fluid sample in the prefiltration layer of the sample application pad;

flowing, by capillary action, the plasma and the free hemoglobin from a sample application site of the colorimetric detection pad to a read portion and control line of the colorimetric detection pad; and visually comparing a color change at the read portion of the colorimetric detection pad to a reference device containing a plurality of reference colors, wherein each reference color corresponds to a different level of free hemoglobin.

Illustrative embodiment 22. The method of any one of Illustrative embodiments 20-21, wherein applying the fluid sample further comprises saturating the hydrophilic receiving surface of the prefiltration layer with the fluid sample, and passing the fluid sample from the prefiltration layer to the filtration layer to saturate the filtration layer with the fluid sample.

Illustrative embodiment 23. The method of any one of Illustrative embodiments 20-22, wherein the hydrophilic receiving surface of the prefiltration layer comprises a plurality of fluid pathways; and wherein applying the fluid sample further comprises saturating the plurality of fluid pathways with the fluid sample, and passing the fluid sample from the prefiltration layer to the filtration layer to saturate the filtration layer with the fluid sample.

Illustrative embodiment 24. The method of any one of Illustrative embodiments 20-23, wherein the colorimetric chamber is defined by a sidewall of the barrel and a cover having a fill pane aligned with the sample application pad and a read pane aligned with the read portion and the control line of the colorimetric detection pad; and wherein applying the fluid sample further comprises viewing the sample application pad through the fill pane of the cover to determine whether the sample application pad is saturated with the fluid sample.

Illustrative embodiment 25. The method of any one of Illustrative embodiments 20-24, wherein the visually comparing step comprises viewing the read portion of the colorimetric detection pad through the read pane of the cover.

Illustrative embodiment 26. An apparatus, comprising:

a barrel having a first end, a second end opposite the first end, an inner surface defining an internal chamber, and a sidewall extending between the first end and the second end, the sidewall defining at least a portion of a colorimetric chamber in fluid communication with the internal chamber via a passage through the sidewall of the barrel, the colorimetric chamber defined by a portion of the sidewall of the barrel and a cover, the cover comprising a housing having an outside surface, an inside surface, and a compression rib extending from the inside surface away from the outside surface; and a colorimetric assay assembly housed in the colorimetric chamber configured to visualize free hemoglobin in a fluid sample, the colorimetric assay assembly comprising:

a sample application pad configured to receive the fluid sample from the internal chamber, wherein the sample application pad is formed of a prefiltration layer of a prefiltration material and a filtration layer of a filtration material, wherein the filtration layer of the sample application pad is porous to plasma and the free hemoglobin and not porous to red blood cells, the compression rib engaging and compressing at least a portion of the prefiltration layer of the sample application pad; and a colorimetric detection pad in fluidic contact with the filtration layer of the sample application pad, the colorimetric detection pad being configured to visualize a presence of the free hemoglobin.

Illustrative embodiment 27. The apparatus of Illustrative embodiment 26, further comprising a fluid path on the inside surface of the cover, the fluid path bounded on at least three sides by the compression rib.

Illustrative embodiment 28. The apparatus of any one of Illustrative embodiments 26-27, further comprising a cavity defined by the inside surface and a wall extending towards the outside surface, the cavity disposed within at least a portion of the fluid path.

Illustrative embodiment 29. The apparatus of any of Illustrative embodiments 26-28, wherein the cover includes a fill pane aligned with the sample application pad to permit viewing the sample application pad through the fill pane, the cavity being at least partially disposed between the compression rib and the fill pane.

Illustrative embodiment 30. The apparatus of any one of Illustrative embodiments 26-29, wherein the cavity is at least partially disposed between the compression rib and the fill pane.

Illustrative embodiment 31. The apparatus of any one of Illustrative embodiments 26-30, wherein the prefiltration layer has one or more edges, and wherein the compression rib engages the prefiltration layer of prefiltration material to compress the prefiltration layer to direct the fluid sample away from the one or more edges of the prefiltration layer when the fluid sample moves within the prefiltration layer.

Illustrative embodiment 32. The apparatus of any one of Illustrative embodiments 26-31, wherein the prefiltration layer has a central region, and wherein the compression rib engages the prefiltration layer to direct the fluid sample toward the central region of the prefiltration layer.

What is claimed is:

1. An apparatus, comprising:

a barrel having a first end, a second end opposite the first end, a sidewall extending between the first end and the second end, and an inner surface defining an internal chamber, the sidewall defining at least a portion of a colorimetric chamber in fluid communication with the internal chamber via a passage through the sidewall of the barrel; and a colorimetric assay assembly housed in the colorimetric chamber configured to detect a presence of free hemoglobin in a fluid sample, the colorimetric assay assembly comprising:

a sample application pad configured to receive the fluid sample from the internal chamber, wherein the sample application pad is formed of a prefiltration layer of a prefiltration material and a filtration layer of a filtration material, wherein the prefiltration layer comprises a distal surface having a first wetting property and a hydrophilic receiving surface having a second wetting property less than the first wetting property, the hydrophilic receiving surface configured to receive the fluid sample and convey at least a portion of the fluid sample to the filtration layer, the filtration layer being porous to plasma and the free hemoglobin and not porous to red blood cells; and a colorimetric detection pad in fluidic contact with the sample application pad, the colorimetric detection pad being configured to visualize a change of color due to the presence of the free hemoglobin.

2. The apparatus of claim 1, wherein the colorimetric chamber is defined by a portion of the sidewall of the barrel and a cover, the cover comprising a housing having an outside surface, an inside surface, and a compression rib extending from the inside surface away from the outside surface, the cover further having a fill pane aligned with the sample application pad for viewing flow of the fluid sample through the sample application pad, and a read pane aligned with a read portion and a control line of the colorimetric detection pad for viewing the read portion and the control line.

3. The apparatus of claim 2, further comprising a cavity defined by the inside surface and a wall extending towards the outside surface, the cavity disposed against at least a portion of the compression rib and within a fluid path bound by the compression rib.

4. The apparatus of claim 3, wherein the cavity is at least partially disposed between the compression rib and the fill pane.

5. The apparatus of claim 2, wherein the prefiltration layer has one or more edges and a central region, and wherein the compression rib engages the prefiltration layer of prefiltration material to compress the prefiltration layer to direct the fluid sample away from the one or more edges of the prefiltration layer and towards the central region of the prefiltration layer when the fluid sample moves within the prefiltration layer.

6. The apparatus of claim 1, wherein the filtration material is an asymmetric polysulfone material.

7. The apparatus of claim 1, wherein the hydrophilic receiving surface of the prefiltration layer further comprises one or more fluid pathway disposed in the hydrophilic receiving surface, each fluid pathway extending from the hydrophilic receiving surface towards the distal surface.

8. The apparatus of claim 7, wherein at least one of the one or more fluid pathway is a perforation extending from the hydrophilic receiving surface through the prefiltration layer towards the distal surface.

9. The apparatus of claim 7, wherein the hydrophilic receiving surface of the prefiltration layer further comprises a first edge, a second edge, a third edge, a fourth edge and a boundary extending from the third edge to the fourth edge thereby forming a modification region on the hydrophilic receiving surface and bound by the first edge, the boundary, the third edge, and the fourth edge, and wherein each fluid pathway is disposed within the modification region.

10. The apparatus of claim 9, wherein at least one of the one or more fluid pathway is a perforation extending from the hydrophilic receiving surface through the prefiltration layer towards the distal surface and wherein each perforation is disposed within the modification region.

11. The apparatus of claim 9, wherein the one or more fluid pathway further extends from the first edge to the boundary within the modification region.

12. The apparatus of claim 10, wherein the one or more fluid pathway has one or more of a square, circular, rectangular, or cross-shaped cross-section geometry.

13. A method comprising:

transferring at least a portion of a fluid sample from a fluid sample collection apparatus to an internal chamber of a barrel via an inlet opening;

passing the portion of the fluid sample from the internal chamber of the barrel to a colorimetric chamber and a colorimetric assay assembly housed in the colorimetric chamber, the colorimetric chamber being in fluid communication with the internal chamber, and the colorimetric assay assembly having a sample application pad and a colorimetric detection pad, the sample application pad is formed of a prefiltration layer comprising a prefiltration material having a hydrophilic receiving surface and a distal surface, the hydrophilic receiving surface having a first wetting property configured to receive the fluid sample from the internal chamber, and the distal surface having a second wetting property being less hydrophilic than the first wetting property, the sample application pad is further formed of a filtration layer comprising a filtration material in fluid communication with the prefiltration layer, the hydrophilic receiving surface being configured to pass plasma, red blood cells, white blood cells, and free hemoglobin;

retaining at least red blood cells from the portion of the fluid sample passing into the colorimetric assay assembly in at least one of the filtration layer and the prefiltration layer of the sample application pad;

indicating, by the colorimetric detection pad of the colorimetric assay assembly, a presence of free hemoglobin in the fluid sample; and transferring the fluid sample from the internal chamber to a liquid sample analyzer with a sample probe responsive to the indication of the presence of free hemoglobin in the fluid sample being below a predetermined threshold.

14. The method of claim 13, wherein indicating the presence of free hemoglobin further comprises:

applying the portion of the fluid sample to the sample application pad of the colorimetric assay assembly and allowing plasma and the free hemoglobin present in the fluid sample to flow through the hydrophilic receiving surface of the prefiltration layer of the sample application pad towards the colorimetric detection pad while retaining at least some red blood cells present in the fluid sample in the prefiltration layer of the sample application pad;

flowing, by capillary action, the plasma and the free hemoglobin from a sample application site of the colorimetric detection pad to a read portion and control line of the colorimetric detection pad; and visually comparing a color change at the read portion and the control line to a reference device containing a plurality of reference colors, wherein each reference color corresponds to a different level of free hemoglobin.

15. The method of claim 14, wherein applying the fluid sample further comprises saturating the hydrophilic receiving surface of the prefiltration layer with the fluid sample, and passing the fluid sample from the prefiltration layer to the filtration layer to saturate the filtration layer with the fluid sample.

16. The method of claim 14, wherein the colorimetric chamber is defined by a sidewall of the barrel and a cover having a fill pane aligned with the sample application pad and a read pane aligned with the read portion and the control line of the colorimetric detection pad; and wherein applying the fluid sample further comprises viewing the sample application pad through the fill pane of the cover to determine whether the sample application pad is saturated with the fluid sample.

17. An apparatus, comprising:

a barrel having a first end, a second end opposite the first end, an inner surface defining an internal chamber, and a sidewall extending between the first end and the second end, the sidewall defining at least a portion of a colorimetric chamber in fluid communication with the internal chamber via a passage through the sidewall of the barrel, the colorimetric chamber defined by a portion of the sidewall of the barrel and a cover, the cover comprising a housing having an outside surface, an inside surface, and a compression rib extending from the inside surface away from the outside surface; and a colorimetric assay assembly housed in the colorimetric chamber configured to visualize free hemoglobin in a fluid sample, the colorimetric assay assembly comprising:

a sample application pad configured to receive the fluid sample from the internal chamber, wherein the sample application pad is formed of a prefiltration layer of a prefiltration material and a filtration layer of a filtration material, wherein the filtration layer of the sample application pad is porous to plasma and the free hemoglobin and not porous to red blood cells, the compression rib engaging and compressing at least a portion of the prefiltration layer of the sample application pad; and a colorimetric detection pad in fluidic contact with the filtration layer of the sample application pad, the colorimetric detection pad being configured to visualize a presence of the free hemoglobin.

18. The apparatus of claim 17, further comprising a fluid path on the inside surface of the cover bounded on at least three sides by the compression rib, and a cavity defined by the inside surface and a wall extending towards the outside surface, the cavity disposed within at least a portion of the fluid path.

19. The apparatus of claim 18, wherein the cover includes a fill pane aligned with the sample application pad to permit viewing the sample application pad through the fill pane, the cavity being at least partially disposed between the compression rib and the fill pane.

20. The apparatus of claim 17, wherein the prefiltration layer has one or more edges and a central region, and wherein the compression rib engages the prefiltration layer of prefiltration material to compress the prefiltration layer to direct the fluid sample away from the one or more edges of the prefiltration layer and towards the central region of the prefiltration layer when the fluid sample moves within the prefiltration layer.

* * * * *